United States Patent [19]
Cheung et al.

[11] Patent Number: 4,892,101
[45] Date of Patent: * Jan. 9, 1990

[54] METHOD AND APPARATUS FOR OFFSETTING BASELINE PORTION OF OXIMETER SIGNAL

[75] Inventors: Peter W. Cheung, Mercer Island; Karl F. Gauglitz, Kirkland; Lee R. Mason, Issaquah; Stephen J. Prosser, Lynnwood; Robert E. Smith, Edmonds; Darrell O. Wagner, Monroe; Scott W. Hunsaker, Seattle, all of Wash.

[73] Assignee: Physio-Control Corporation, Redmond, Wash.

[*] Notice: The portion of the term of this patent subsequent to Apr. 11, 2006 has been disclaimed.

[21] Appl. No.: 315,330

[22] Filed: Feb. 24, 1989

Related U.S. Application Data

[63] Continuation of Ser. No. 897,664, Aug. 18, 1986, Pat. No. 4,819,646.

[51] Int. Cl.$^4$ .......................... A61B 5/00; A61B 6/00
[52] U.S. Cl. .................................... 128/633; 128/664; 128/666; 356/41
[58] Field of Search ................. 128/633, 634, 664-667; 356/41

[56] References Cited

U.S. PATENT DOCUMENTS

| | | |
|---|---|---|
| 2,706,927 | 4/1955 | Wood . |
| 3,430,106 | 2/1967 | McDowell . |
| 3,709,612 | 1/1973 | Clemens . |
| 4,086,915 | 5/1978 | Kofsky et al. . |
| 4,167,331 | 9/1979 | Nielsen . |
| 4,188,551 | 2/1980 | Iwasaki et al. . |
| 4,586,513 | 5/1986 | Hamaguri . |
| 4,639,134 | 1/1987 | Bletz . |
| 4,759,369 | 7/1988 | Taylor . |
| 4,819,646 | 4/1989 | Cheung et al. ................. 128/664 |

FOREIGN PATENT DOCUMENTS 83304939.8  8/1983  European Pat. Off. .

Primary Examiner—Max Hindenburg
Assistant Examiner—John C. Hanley
Attorney, Agent, or Firm—Christensen, O'Connor, Johnson & Kindness

[57] ABSTRACT

A feedback control system is disclosed for use in processing signals employed in pulse transmittance oximetry. The signals are produced in response to light transmitted through, for example, a finger at two different wavelengths. Each signal includes a slowly varying baseline component representing the relatively fixed attenuation of light produced by bone, tissue, skin, and hair. The signals also include pulsatile components representing the attenuation produced by the changing blood volume and oxygen saturation within the finger. The signals are processed by the feedback control system before being converted by an analog-to-digital (A/D) converter (72) for subsequent analysis by a microcomputer (16). The feedback control system includes a controllable offset subtractor (66), a programmable gain amplifier (68), controllable drivers (44) for the light sources (40, 42), and the microcomputer (16). The microcomputer (16) receives signals from the offset subtractor (66), gain amplifier (68), drivers (44) and A/D converter (72) to produce signals that control the function of the subtractor (66) and drivers (44) in the following manner. Normally, the drivers (44) are maintained within a predetermined current range. In the event the microcomputer (16) senses an output from the converter (72) that is not within a predetermined range, the drive signal is adjusted to produce an acceptable signal. The magnitude of the offset removed by the subtractor (66), as controlled by the microcomputer (16), is maintained at a constant level when the converter (72) output is within a first predetermined range and is a predetermined function of the converter (72) output when that output falls within a second predetermined range.

9 Claims, 17 Drawing Sheets

METHOD AND APPARATUS FOR OFFSETTING BASELINE PORTION OF OXIMETER SIGNAL

This is a continuation of the prior application Ser. No. 897,664, filed Aug. 18, 1986, now U.S. Pat. No. 4,819,646, the benefit of the filing date of which is hereby claimed under 35U.S.C.120.

BACKGROUND OF THE INVENTION

This invention relates to oximetry and, more particularly, to signal-processing techniques employed in oximetry.

The arterial oxygen saturation and pulse rate of an individual may be of interest for a variety of reasons. For example, in the operating room up-to-date information regarding oxygen saturation can be used to signal changing physiological factors, the malfunction of anaesthesia equipment, or physician error. Similarly, in the intensive care unit, oxygen saturation information can be used to confirm the provision of proper patient ventilation and allow the patient to be withdrawn from a ventilator at an optimal rate.

In many applications, particularly including the operating room and intensive care unit, continual information regarding pulse rate and oxygen saturation is important if the presence of harmful physiological conditions is to be detected before a substantial risk to the patient is presented. A noninvasive technique is also desirable in many applications, for example, when a home health care nurse is performing a routine checkup, because it increases both operator convenience and patient comfort. Pulse transmittance oximetry is addressed to these problems and provides noninvasive, continual information about pulse rate and oxygen saturation. The information produced, however, is only useful when the operator can depend on its accuracy. The method and apparatus of the present invention are, therefore, directed to the improved accuracy of such information without undue cost.

As will be discussed in greater detail below, pulse transmittance oximetry basically involves measurement of the effect arterial blood in tissue has on the intensity of light passing therethrough. More particularly, the volume of blood in the tissue is a function of the arterial pulse, with a greater volume present at systole and a lesser volume present at diastole. Because blood absorbs some of the light passing through the tissue, the intensity of the light emerging from the tissue is inversely proportional to the volume of blood in the tissue. Thus, the emergent light intensity will vary with the arterial pulse and can be used to indicate a patient's pulse rate. In addition, the absorption coefficient of oxyhemoglobin (hemoglobin combined with oxygen, $HbO_2$) is different from that of deoxygenated hemoglobin (Hb) for most wavelengths of light. For that reason, differences in the amount of light absorbed by the blood at two different wavelengths can be used to indicate the hemoglobin oxygen saturation, % $SaO_2$ (OS), which equals $([HBO_2]/([Hb]+[HbO_2])) \times 100\%$. Thus, measurement of the amount of light transmitted through, for example, a finger can be used to determine both the patient's pulse rate and hemoglobin oxygen saturation.

As will be appreciated, the intensity of light transmitted through a finger is a function of the absorption coefficient of both "fixed" components, such as bone, tissue, skin, and hair, as well as "variable" components, such as the volume of blood in the tissue. The intensity of light transmitted through the tissue, when expressed as a function of time, is often said to include a baseline component, which varies slowly with time and represents the effect of the fixed components on the light, as well as a periodic pulsatile component, which varies more rapidly with time and represents the effect that changing tissue blood volume has on the light. Because the attenuation produced by the fixed tissue components does not contain information about pulse rate and arterial oxygen saturation, the pulsatile signal is of primary interest. In that regard, many of the prior art transmittance oximetry techniques eliminate the so-called "DC" baseline component from the signal analyzed.

For example, in U.S. Pat. No. 2,706,927 (Wood) measurements of light absorption at two wavelengths are taken under a "bloodless" condition and a "normal" condition. In the bloodless condition, as much blood as possible is squeezed from the tissue being analyzed. Then, light at both wavelengths is transmitted through the tissue and absorption measurements made. These measurements indicate the effect that all nonblood tissue components have on the light. When normal blood flow has been restored to the tissue, a second set of measurements is made that indicates the influence of both the blood and nonblood components. The difference in light absorption between the two conditions is then used to determine the average oxygen saturation of the tissue, including the effects of both arterial and venous blood. As will be readily apparent, this process basically eliminates the DC, nonblood component from the signal that the oxygen saturation is extracted from.

For a number of reasons, however, the Wood method fails to provide the necessary accuracy. For example, a true bloodless condition is not practical to obtain. In addition, efforts to obtain a bloodless condition, such as by squeezing the tissue, may result in a different light transmission path for the two conditions. In addition to problems with accuracy, the Wood approach is both inconvenient and time consuming.

A more refined approach to pulse transmittance oximetry is disclosed in U.S. Pat. No. 4,086,915 (Kofsky et al.). The Kofsky et al. reference is of interest for two reasons. First, the technique employed automatically eliminates the effect that fixed components in the tissue have on the light transmitted therethrough, avoiding the need to produce bloodless tissue. More particularly, as developed in the Kofsky et al. reference from the Beer-Lambert law of absorption, the derivatives of the intensity of the light transmitted through the tissue at two different wavelengths, when multiplied by predetermined pseudocoefficients, can be used to determine oxygen saturation. Basic mathematics indicate that such derivatives are substantially independent of the DC component of the intensity. The pseudocoefficients are determined through measurements taken during a calibration procedure in which a patient first respires air having a normal oxygen content and, later, respires air of a reduced oxygen content. As will be appreciated, this calibration process is at best cumbersome.

The second feature of the Kofsky et al. arrangement that is of interest is its removal of the DC component of the signal prior to being amplified for subsequent processing. More particularly, the signal is amplified to allow its slope (i.e., the derivative) to be more accurately determined. To avoid amplifier saturation, a portion of the relatively large DC component of the signal is removed prior to amplification. To accomplish this removal, the signal from the light detector is applied to the two inputs of a differential amplifier as follows. The signal is directly input to the positive terminal of the amplifier. The signal is also passed through a low-resolution A/D converter, followed by a D/A converter, before being input to the negative terminal of the amplifier. The A/D converter has a resolution of approximately 1/10 that of the input signal. For example, if the signal is at 6.3 volts, the output of the A/D converter would be 6 volts. Therefore, the output of the converter represents a substantial portion of the signal, which typically can be used to approximate the DC signal level. Combination of that signal with the directly applied detector signal at the amplifier produces an output that can be used to approximate the AC signal. As will be readily appreciated, however, the process may be relatively inaccurate because the output of the A/D converter is often a poor indicator of the DC signal.

U.S. Pat. No. 4,167,331 (Nielson) discloses another pulse transmittance oximeter. The disclosed oximeter is based upon the principle that the absorption of light by a material is directly proportional to the logarithm of the light intensity after having been attenuated by the absorber, as derived from the Beer-Lambert law. The oximeter employs light-emitting diodes (LEDs) to produce light at red and infrared wavelengths for transmission through tissue. A photosensitive device responds to the light produced by the LEDs and attenuated by the tissue, producing an output current. That output current is amplified by a logarithmic amplifier to produce a signal having AC and DC components and containing information about the intensity of light transmitted at both wavelengths. Sample-and-hold circuits demodulate the red and infrared wavelength signals. The DC components of each signal are then blocked by a series bandpass amplifier and capacitors, eliminating the effect of the fixed absorptive components from the signal. The resultant AC signal components are unaffected by fixed absorption components, such as hair, bone, tissue, skin. An average value of each AC signal is then produced. The ratio of the two averages is then used to determine the oxygen saturation from empirically determined values associated with the ratio. The AC components are also used to determine the pulse rate.

Another reference addressed to pulse transmittance oximetry is U.S. Pat. No. 4,407,290 (Wilber). In that reference, light pulses produced by LEDs at two different wavelengths are applied to, for example, an earlobe. A sensor responds to the light transmitted through the earlobe, producing a signal for each wavelength having a DC and AC component resulting from the presence of constant and pulsatile absorptive components in the earlobe. A normalization circuit employs feedback to scale both signals so that the DC nonpulsatile components of each are equal and the offset voltages removed. Decoders separate the two signals, so controlled, into channels A and B where the DC component from each is removed. The remaining AC components of the signals are amplified and combined at a multiplexer prior to analog-to-digital (A/D) conversion. Oxygen saturation is determined by a digital processor in accordance with the following relationship:

$$OS = \frac{X_1 R(\lambda_1) + X_2 R(\lambda_2)}{X_3 R(\lambda_1) + X_4 R(\lambda_2)}$$

wherein empirically derived data for the constants $X_1$, $X_2$, $X_3$ and $X_4$ is stored in the processor.

European patent application No. 83304939.8 (New, Jr. et al.) discloses an additional pulse transmittance oximeter. Two LEDs expose a body member, for example, a finger, to light having red and infrared wavelengths, with each LED having a one-in-four duty cycle. A detector produces a signal in response that is then split into two channels. The one-in-four duty cycle allows negatively amplified noise signals to be integrated with positively amplified signals including the detector response and noise, thereby eliminating the effect of noise on the signal produced. The resultant signals include a substantially constant DC component and a pulsatile AC component. To improve the accuracy of a subsequent analog-to-digital (A/D) conversion, a fixed DC value is subtracted from the signal prior to the conversion. This level is then added back in by a microprocessor after the conversion. Logarithmic analysis is avoided by the microprocessor in the following manner. For each wavelength of light transmitted through the finger, a quotient of the pulsatile component over the constant component is determined. The ratio of the two quotients is then determined and fitted to a curve of independently derived oxygen saturations. To compensate for the different transmission characteristics of different patients' fingers, an adjustable drive source for the LEDs is provided. In addition, an apparatus for automatically caibrating the device is disclosed.

Prior art oximeters have, however, not always employed signal-processing techniques that are adequate to provide maximum resolution of the signal received for analysis. As a result, the accuracy of oxygen saturation and pulse rate determinations made by the oximeter may suffer. The disclosed invention addresses this problem and improves the accuracy previously attainable in the art of oximetry.

SUMMARY OF THE INVENTION

The present invention discloses an apparatus for processing signals produced by a sensor that contain information about the oxygen saturation of arterial blood flowing in tissue. The apparatus includes an offset subtractor for subtracting a controlled portion of the sensor signal from that signal. The offset subtractor produces an output substantially equal to the portion of the sensor signal remaining after the controlled portion has been subtracted therefrom. The system also includes a controller, coupled to the offset subtractor, which receives the output of the offset subtractor and produces a subtraction control signal dependent upon that output. The subtraction control signal is transferred to the offset subtractor and determines the magnitude of the controlled portion of the signal subtracted thereby. An analyzer receives the output of the offset subtractor and produces an indication of the oxygen saturation of the arterial blood.

In accordance with a particular aspect of the invention, the controlled portion of the detector signal subtracted is held constant when the absolute value of the offset subtractor output is less than a first predetermined level. When the absolute value of the offset subtractor output falls within a predetermined range above that level, however, a subtraction control signal is produced indicating that the offset subtractor is to adjust the magnitude of the controlled portion by an amount proportional to the magnitude of the offset subtractor ouput.

When the absolute value of the offset subtractor output exceeds a second predetermined level, a subtraction control signal is produced indicating that the offset subtractor is no longer able to adjust the controlled portion of the signal to be subtracted. Preferably, the controlled portion subtracted from the detector signal by the offset subtractor is initialized at a predetermined value.

In accordance with another aspect of the invention, the system further includes a controllable gain amplifier for amplifying the output of the offset subtractor by a controlled gain. The amplifier produces an output that is substantially equal to the product of the offset subtractor output and the gain. The controller produces an amplifier control signal that is received by the amplifier, which adjusts the controlled gain in response thereto.

In accordance with a further aspect of the invention, the controller produces a sensor control signal to which said sensor responds. The controller establishes the sensor control signal at a level sufficient to cause the sensor signal to fall within a predetrmined sensor signal range.

In accordance with further aspects of this invention, a differential current-to-voltage amplifier amplifies the sensor signal before it is received by the offset subtractor. An analog-to-digital converter also converts the output of the controllable-gain amplifier into a digital format for analysis. The analyzer removes the gain and adds the controlled portion back to the amplifier output before producing the indication of oxygen saturation.

As will be appreciated, the disclosed invention also includes an oximeter employing the apparatus described above in conjunction with a sensor. The sensor includes a light source that responds to a control signal from the controller and illuminates the tissue. The intensity of the illumination is determined by the control signal. A detector included in the sensor responds to the illumination of the tissue by producing a signal that contains information about the oxygen saturation of the arterial blood. A red optical filter may be included to filter the light received by the detector.

As will also be appreciated, the disclosed invention includes the method of processing signals employed by the apparatus discussed above to determine the oxygen saturation of arterial blood flowing in tissue. In a basic form, the method includes the steps of subtracting from the sensor signal a controlled portion of the signal in response to a subtraction control signal. A subtraction output is produced that substantially equals the portion of the sensor signal remaining after the controlled portion has been subtracted therefrom. A subtraction control signal is also produced, dependent on the subtraction output in a manner indicating the desired adjustment in the controlled portion subtracted from the sensor signal.

BRIEF DESCRIPTION OF THE DRAWINGS

The invention can best be understood by reference to the following portion of the specification, taken in conjunction with the accompanying drawings in which:

FIG. 26 illustrates a calibrated offset table stored in the microcomputer for use in adjusting the operation of the I/O circuit.

DETAILED DESCRIPTION

Figure 1:
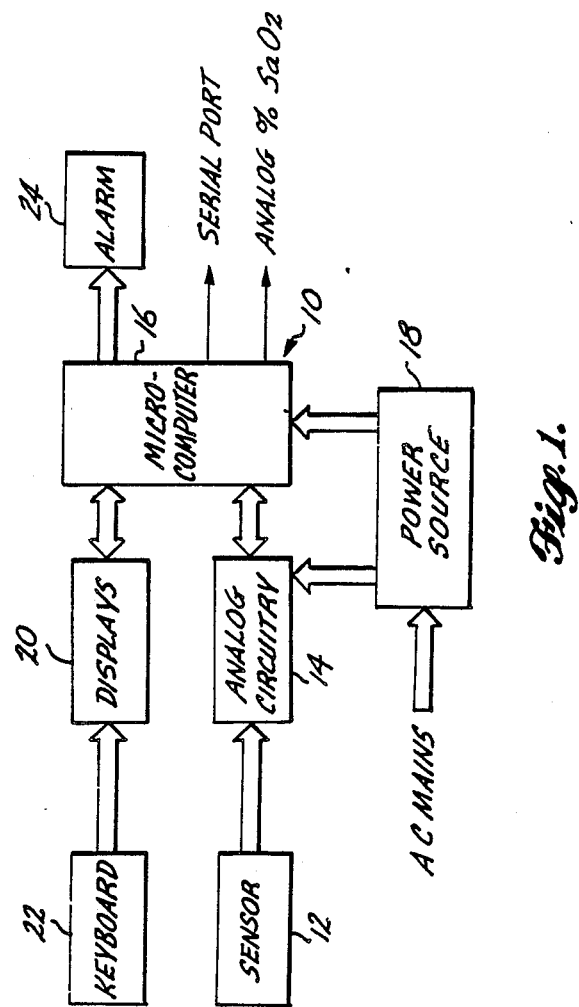
FIG. 1 is a block diagram of an oximeter including a sensor, input/output (I/O) circuit, microcomputer, alarm, displays, power supply, and keyboard.

Referring to the overall system block diagram shown in FIG. 1, a pulse transmittance oximeter 10 employing this invention includes a sensor 12, input/output (I/O) circuit 14, microcomputer 16, power source 18, display 20, keyboard 22 and alarm 24. Before discussing these elements in detail, however, an outline of the theoretical basis of pulse transmittance oximetry as practiced by the oximeter of FIG. 1 is provided.

An understanding of the relevant theory begins with a discussion of the Beer-Lambert law. This law governs the absorption of optical radiation by homogeneous absorbing media and can best be understood with reference to FIGS. 2 and 3 in the following manner.

Figure 2:
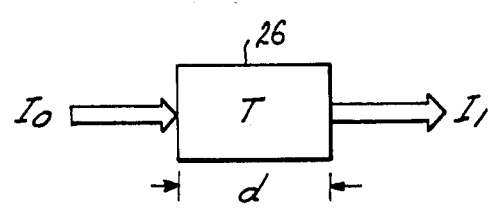
FIG. 2 is a block diagram illustrating the transmission of light through an absorptive medium.
Figure 3:
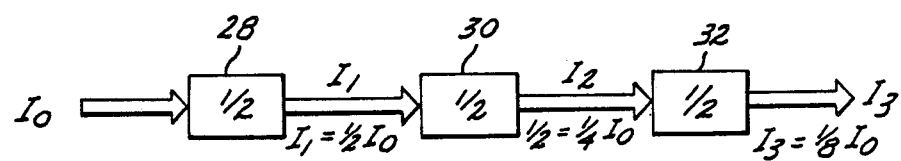
FIG. 3 is a block diagram illustrating the transmission of light through the absorptive medium of FIG. 2, wherein the medium is broken up into elemental components.

As shown in FIG. 2, incident light having an intensity $I_0$ impinges upon an absorptive medium 26. Medium 26 has a characteristic absorbance factor A that indicates the attenuating affect medium 26 has on the incident light. Similarly, a transmission factor T for the medium is defined as the reciprocal of the absorbance factor, $1/A$. The intensity of the light $I_1$ emerging from medium 26 is less than $I_0$ and can be expressed functionally as the product $TI_0$. With medium 26 divided into a number of identical components, each of unit thickness (in the direction of light transmission) and the same transmission factor T, the effect of medium 26 on the incident light $I_0$ is as shown in FIG. 3.

There, medium 26 is illustrated as consisting of three components 28, 30, and 32. As will be appreciated, the intensity $I_1$ of the light emerging from component 28 is equal to the incident light intensity $I_0$ multiplied by the transmission factor T. Component 30 has a similar effect on light passing therethrough. Thus, because the light incident upon component 30 is equal to the product $TI_0$, the emergent light intensity $I_2$ is equal to the product $TI_1$ or $T^2I_0$. Component 32 has the same effect on light and, as shown in FIG. 3, the intensity of the emergent light $I_3$ for the entire medium 26 so modeled is equal to the product $TI_2$ or $T^3I_0$. If the thickness d of medium 26 is n unit lengths, it can be modeled as including n identical components of unit thickness. It will then be appreciated that the intensity of light emerging from medium 26 can be designated $I_n$ and the product is equal to $T^nI_0$. Expressed as a function of the absorbance constant A, $I_n$ can also be written as the product $(1/A^n)I_0$.

From the preceding discussion, it will be readily appreciated that the absorptive effect of medium 26 on the intensity of the incident light $I_0$ is one of exponential decay. Because A may be an inconvenient base to work with, $I_n$ can be rewritten as a function of a more convenient base, b, by recognizing that $A^n$ is equal to $b^{\alpha n}$, where $\alpha$ is the absorbance of medium 26 per unit length. The term $\alpha$ is frequently referred to as the relative extinction coefficient and is equal to $\log_b A$.

Figure 4:
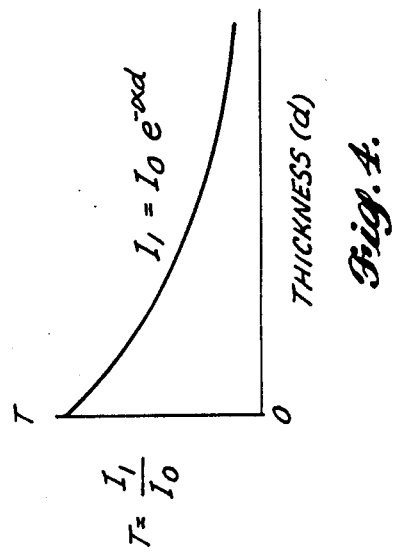
FIG. 4 is a graphical comparison of the incident light intensity to the emergent light intensity as modeled in FIG. 2.

Given the preceding discussion, it will be appreciated that the intensity of the light $I_n$ emerging from medium 26 can be expressed in base 10 (where $\alpha = \alpha_1$) as $I_0 10^{-\alpha_1 n}$, or in base e (where $\alpha = \alpha_2$) as $I_0 e^{-\alpha_2 n}$. The effect that the thickness of medium 26 has on the emergent light intensity $I_n$ is graphically depicted in FIG. 4. If the light incident upon medium 26 is established as having unit intensity, FIG. 4 also represents the transmission factor T of the entire medium as a function of thickness.

The discussion above can be applied generally to the medium 26 shown in FIG. 2 to produce:

$$I_1 = I_0 e^{-\alpha d} \qquad (1)$$

where $I_1$ is the emergent light intensity, $I_0$ is the incident light intensity, $\alpha$ is the absorbance coefficient of the medium, d is the thickness of the medium per unit length in unit lengths, and the exponential nature of the relationship has arbitrarily been expressed in terms of base e. Equation (1) is commonly referred to as the Beer-Lambert law of exponential light decay through a homogeneous absorbing medium.

Figure 5:
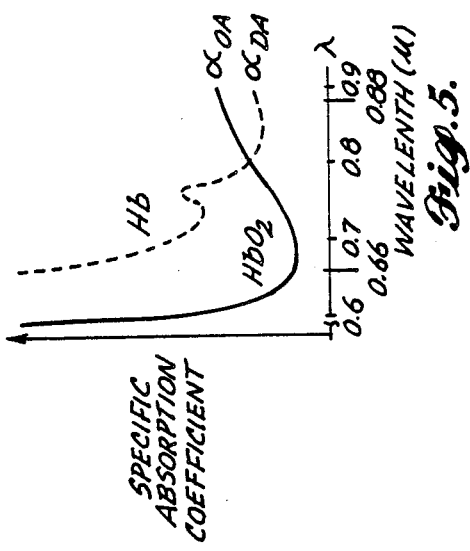
FIG. 5 is a graphical comparison of the specific absorption coefficients for oxygenated hemoglobin and deoxygenated hemoglobin as a function of the wavelength of light transmitted therethrough.

With this basic understanding of the Beer-Lambert law, a discussion of its application to the problems of pulse rate and hemoglobin oxygen saturation measurement is now presented. As shown in FIG. 5, the absorption coefficients for oxygenated and deoxygenated hemoglobin are different at every wavelength, except an isobestic wavelength. Thus, it will be appreciated that if a person's finger is exposed to incident light and the emergent light intensity measured, the difference in intensity between the two, which is the amount of light absorbed, contains information relating to the oxygenated hemoglobin content of the blood in the finger. The manner in which this information is extracted from the Beer-Lambert law is discussed below. In addition, it will be appreciated that the volume of blood contained within an individual's finger varies with the individual's pulse. Thus, the thickness of the finger also varies slightly with each pulse, creating a changing path length for light transmitted through the finger. Because a longer lightpath allows additional light to be absorbed, time-dependent information relating to the difference between the incident and emergent light intensities can be used to determine the individual's pulse. The manner in which this information is extracted from the Beer-Lambert law is also discussed below.

As noted in the preceding paragraph, information about the incident and emergent intensities of light transmitted through a finger can be used to determine oxygen saturation and pulse rate. The theoretical basis for extracting the required information, however, is complicated by several problems. For example, the precise intensity of the incident light applied to the finger is not easily determined. Thus, it may be necessary to extract the required information independently of the intensity of the incident light. Further, because the changing volume of blood in the finger and, hence, thickness of the lightpath therethrough, are not exclusively dependent upon the individual's pulse, it is desirable to eliminate the changing path length as a variable from the computations.

Figure 6:
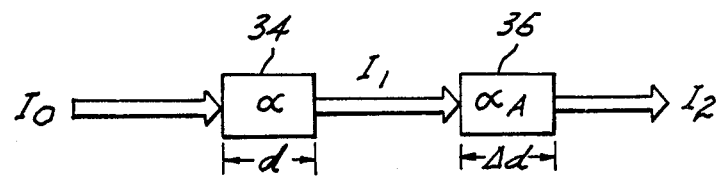
FIG. 6 is a block diagram illustrating the transmission of light through a block model of the components of a finger.

The manner in which the Beer-Lambert law is refined to eliminate the incident intensity and path length as variables is as follows. With reference to FIG. 6, a human finger is modeled by two components 34 and 36, in a manner similar to that shown in FIG. 3. Baseline component 34 models the unchanging absorptive elements of the finger. This component includes, for example, bone, tissue, skin, hair, and baseline venous and arterial blood and has a thickness designated d and an absorbance $\alpha$.

Pulsatile component 36 represents the changing absorptive portion of the finger, the arterial blood volume. As shown, the thickness of this component is designated $\Delta d$, representing the variable nature of the thickness, and the absorbance of this arterial blood component is designated $\alpha_A$ representing the arterial blood absorbance.

As will be appreciated from the earlier analysis with respect to FIG. 3, the light $I_1$ emerging from component 34 can be written as a function of the incident light intensity $I_0$ as follows:

$$I_1 = I_0 e^{-\alpha d} \qquad (2)$$

Likewise, the intensity of light $I_2$ emerging from component 36 is a function of its incident light intensity $I_1$, and:

$$I_2 = I_1 e^{-\alpha_A \Delta d} \qquad (3)$$

Substitution of the expression for $I_1$ developed in equation (2) for that used in equation (3), when simplified, results in the following expression for the intensity $I_2$ of light emerging from the finger as a function of the intensity of light $I_0$ incident upon the finger;

$$I_2 = I_0 e^{-[\alpha d + \alpha_A \Delta d]} \quad (4)$$

Because our interest lies in the effect on the light produced by the arterial blood volume, the relationship between $I_2$ and $I_1$ is of particular interest. Defining the change in transmission produced by the arterial component 36 as $T_{\Delta A}$, we have:

$$T_{\Delta A} = I_2/I_1 \quad (5)$$

Substituting the expressions for $I_1$ and $I_2$ obtained in equations (2) and (3), respectively, equation (5) becomes:

$$T_{\Delta A} = \frac{I_0 e^{-[\alpha d + \alpha_A \Delta d]}}{I_0 e^{-\alpha d}} \quad (6)$$

It will be appreciated that the $I_0$ term can be cancelled from both the numerator and denominator of equation (6), thereby eliminating the input light intensity as a variable in the equation. With equation (6) fully simplified, the change in arterial transmission can be expressed as:

$$T_{\Delta A} = e^{-\alpha_A \Delta d} \quad (7)$$

A device employing this principle of operation is effectively self-calibrating, being independent of the incident light intensity $I_0$.

At this point, a consideration of equation (7) reveals that the changing thickness of the finger, $\Delta d$, produced by the changing arterial blood volume still remains as a variable. The $\Delta d$ variable is eliminated in the following manner. For convenience of expression, the logarithms of the terms in equation (7) are produced with respect to the same base originally employed in equation (1). Thus, equation (7) becomes:

$$\ln T_{\Delta A} = \ln (e^{-\alpha_A \Delta d}) = -\alpha_A \Delta d \quad (8)$$

A preferred technique for eliminating the $\Delta d$ variable utilizes information drawn from the change in arterial transmission experienced at two wavelenths.

The particular wavelengths selected are determined in part by consideration of a more complete expression of the arterial absorbance $\alpha_A$:

$$\alpha_A = (\alpha_{OA})(OS) - (\alpha_{DA})(1 - OS) \quad (9)$$

where $\alpha_{OA}$ is the oxygenated arterial absorbance, $\alpha_{DA}$ is the deoxygenated arterial absorbance, and OS is the hemoglobin oxygen saturation of the arterial blood volume. As will be appreciated from FIG. 5, $\alpha_{OA}$ and $\alpha_{DA}$ are substantially unequal at all light wavelengths in the red and near-infrared wavelength regions except for an isobestic wavelength occurring at approximately 805 nanometers. With an arterial oxygen saturation OS of approximately 90 percent, it will be appareciated from equation (9) that the arterial absorbance $\alpha_A$ is 90 percent attributable to the oxygenated arterial absorbance $\alpha_{OA}$ and 10 percent attributable to the deoxygenated arterial absorbance $\alpha_{DA}$. At the isobestic wavelength, the relative contribution of these two coefficients to the arterial absorbance $\alpha_A$ is of minimal significance in that both $\alpha_{OA}$ and $\alpha_{DA}$ are equal. Thus, a wavelength roughly approximating the isobestic wavelength of the curves illustrated in FIG. 5 is a convenient one for use in eliminating the change in finger thickness $\Delta d$ attributable to arterial blood flow.

A second wavelength is selected at a distance from the approximately isobestic wavelength that is sufficient to allow the two signals to be easily distinguished. In addition, the relative difference of the oxygenated and deoxygenated arterial absorbances at this wavelength is more pronounced. In light of the foregoing considerations, it is generally preferred that the two wavelengths selected fall within the red and infrared regions of the electromagnetic spectrum.

The foregoing information, when combined with equation (8) is used to produce the following ratio:

$$\frac{\ln T_{\Delta AR}}{\ln T_{\Delta AIR}} = \frac{-\alpha_A \Delta d @ \lambda_R}{-\alpha_A \Delta d @ \lambda_{IR}} \quad (10)$$

where $T_{\Delta AR}$ equals the change in arterial transmission of light at the red wavelength $\lambda_R$ and $T_{\Delta AIR}$ is the change in arterial transmission at the infrared wavelength $\lambda_{IR}$. It will be appreciated that if two sources are positioned at substantially the same location on the finger, the length of the lightpath through the finger is substantially the same for the light emitted by each. Thus, the change in the lightpath resulting from arterial blood flow, $\Delta d$, is substantially the same for both the red and infrared wavelength sources. For that reason, the $\Delta d$ term in the numerator and denominator of the right-hand side of equation (10) cancel, producing:

$$\frac{\ln T_{\Delta AR}}{\ln T_{\Delta AIR}} = \frac{\alpha_A @ \lambda_R}{\alpha_A @ \lambda_{IR}} \quad (11)$$

As will be appreciated, equation (11) is independent of both the incident light intensity $I_0$ and the change in finger thickness $\Delta d$ attributable to arterial blood flow. The foregoing derivations form the theoretical basis of pulse oximetry measurement. Because of the complexity of the physiological process, however, the ratio indicated in equation (11) does not directly provide an accurate measurement of oxygen saturation. The correlation between the ratio of equation (11) and actual arterial blood gas measurements is, therefore, relied on to produce an indication of the oxygen saturation. Thus, if the ratio of the arterial absorbance at the red and infrared wavelengths can be determined, the oxygen saturation of the arterial blood flow can be extracted from independently derived, empirical calibration curves in a manner independent of $I_0$ and $\Delta d$.

For simplicity, a measured ratio $R_{OS}$ is defined from equation (11) as:

$$\text{Ratio} = R_{OS} = \frac{\alpha_A @ \lambda_R}{\alpha_A @ \lambda_{IR}} \quad (12)$$

Figure 7:
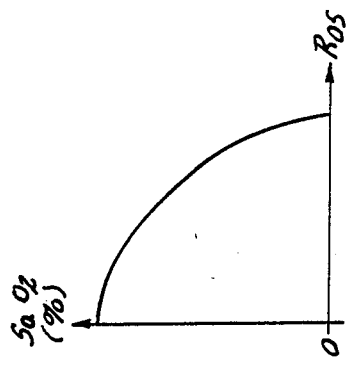
FIG. 7 is a graphical comparison of empirically derived oxygen saturation measurement with a variable that is measurable by the oximeter.

It is this measured value for $R_{OS}$ that is plotted on the x-axis of independently derived oxygen saturation curves, as shown in FIG. 7 and discussed in greater detail below, with the hemoglobin oxygen saturation being referenced on the y-axis.

Figure 9:
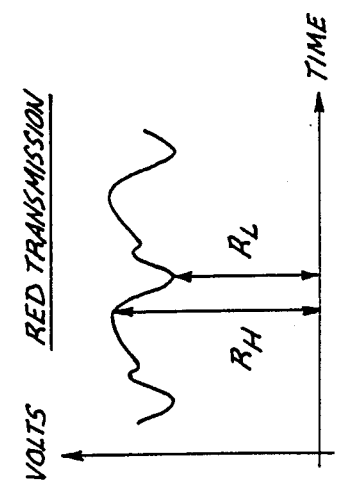
FIG. 9 is a graphical plot as a function of time of the transmittance of light at the red wavelength through the finger.
Figure 8:
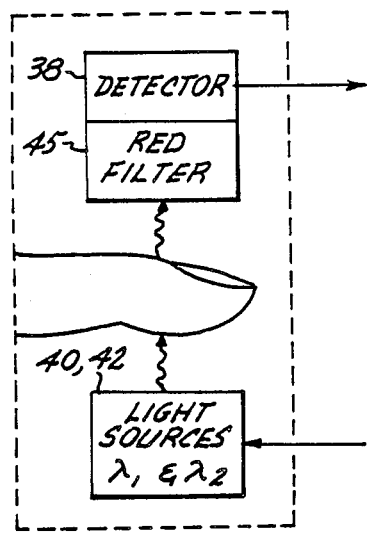
FIG. 8 is a schematic illustration of the transmission of light at two wavelengths through a finger in accordance with the invention.

Measurement of the arterial absorbances at both wavelengths is performed in the following manner. As shown in FIG. 8, a detector 38 placed on the side of a finger opposite red and infrared wavelength light sources 40 and 42 receives light at both wavelengths transmitted through the finger. As shown in FIG. 9, the received red wavelength light intensity, plotted as a function of time, varies with each pulse, and has high and low values $R_H$ and $R_L$, respectively. $R_L$ occurs substantially at systole, when arterial blood volume is at its greatest; while $R_H$ occurs substantially at diastole, when the arterial blood volume is lowest. From the earlier discussion of the exponential light decay through homogeneous media, it will be appreciated that:

$$R_L = I_0 e^{-[\alpha d + \alpha_A \Delta d]} @ \lambda_R \quad (13)$$

Similarly:

$$R_H = I_0 e^{-\alpha d} @ \lambda_R \quad (14)$$

Taking the ratio of equations (13) and (14) and simplifying, we have:

$$\frac{R_L}{R_H} = I_0 \frac{e^{-[\alpha d + \alpha_A \Delta d]}}{I_0 e^{-\Delta d}} @ \lambda_R = e^{-\alpha_A \Delta d} @ \lambda_R \quad (15)$$

Taking the logarithm of both sides of equation (15) produces:

$$\ln(R_L/R_H) = \ln(e^{-\alpha_A \Delta d}) @ \lambda_R = -\alpha_A \Delta d @ \lambda_R \quad (16)$$

As will be readily appreciated, similar expression can be produced for the signals representative of the infrared wavelength light received by detector 38. Thus, the minimum light intensity passing through the finger at the infrared wavelengtcan be written:

$$IR_L = I_0 e^{-[\alpha d + \alpha_A \Delta d]} @ \lambda_{IR} \quad (17)$$

Similarly, the maximum light intensity emerging from the finger at the infrared wavelength can be expressed as:

$$IR_H = I_0 e^{-\alpha d} @ \lambda_{IR} \quad (18)$$

The ratio of the terms in equations (17) and (18) can be expressed as:

$$\frac{IR_L}{IR_H} = \frac{I_0 e^{-[\alpha d + \alpha_A \Delta d]}}{I_0 e^{-\alpha d}} @ \lambda_{IR} = e^{-\alpha_A \Delta d} @ \lambda_{IR} \quad (19)$$

Use of logarithms simplifies equation (19) to:

$$\ln(IR_L/IR_H) = \ln(e^{-\alpha_A \Delta d}) @ \lambda_{IR} = -\alpha_A \Delta d @ \lambda_{IR} \quad (20)$$

The ratiometric combination of equations (16) and (20) yields:

$$\frac{\ln(R_L/R_H)}{\ln(IR_L/IR_H)} = \frac{-\alpha_A \Delta d @ \lambda_R}{-\alpha_A \Delta d @ \lambda_{IR}} \quad (21)$$

Because the $\Delta d$ term in the numerator and denominator of the right-hand side of equation (21) cancel, as do the negative signs before each term, it will be appreciated that equation (21) when combined with equation (12) yields:

$$\text{Ratio} = R_{OS} = \frac{\alpha_A @ \lambda_R}{\alpha_A @ \lambda_{IR}} = \quad (22)$$

$$\frac{\ln(R_L/R_H)}{\ln(IR_L/IR_H)} = \frac{\ln(R_H/R_L)}{\ln(IR_H/IR_L)}$$

Thus, by measuring the minimum and maximum emergent light intensities at both the red and infrared wavelengths ($R_L$, $R_H$, $IR_L$, $IR_H$), a value for the term $R_{OS}$ can be computed. From this, empirically derived calibration curves similar to that shown in FIG. 7 can be used to determine the oxygen saturation as described in greater detail in conjunction with the discussion of the various components of oximeter 10 that follows. As will be appreciated, the determination of oxygen saturation in this manner differs from prior art techniques, such as that disclosed by Wilber, by performing measurements based upon both the baseline and pulsatile components of the signals.

The first component of oximeter 10 to be discussed is sensor 12. The function of sensor 12 is substantially to provide the desired orientation of light sources 40 and 42, for example, light-emitting diodes (LEDs), and light detector 38 with respect to a suitable portion of a patient's body. For example, the sensor must align LEDs 40 and 42 with detector 38 in a manner such that the path of light from each LED to the detector 38 is substantially the same distance. In addition, the path must traverse a portion of the patient's body through which a usable amount of light is passed, for example, a finger, toe, earlobe, or the nasal septum. Because changes in the lightpath can significantly affect the readings taken, as noted above, the sensor must maintain the position of LEDs 40 and 42 and detector 38 with respect to the transmission path through the patient's skin at all times. Otherwise, signal fluctuations known as motion-artifact may be produced. In addition, the sensor should apply only insubstantial pressure to the patient's skin and underlying tissue. Otherwise, normal arterial blood flow upon which the pulse oximeter relies for accurate operation, may be disrupted. Finally, the sensor should be quickly attachable to the patient and should cause no discomfort.

Figure 11:
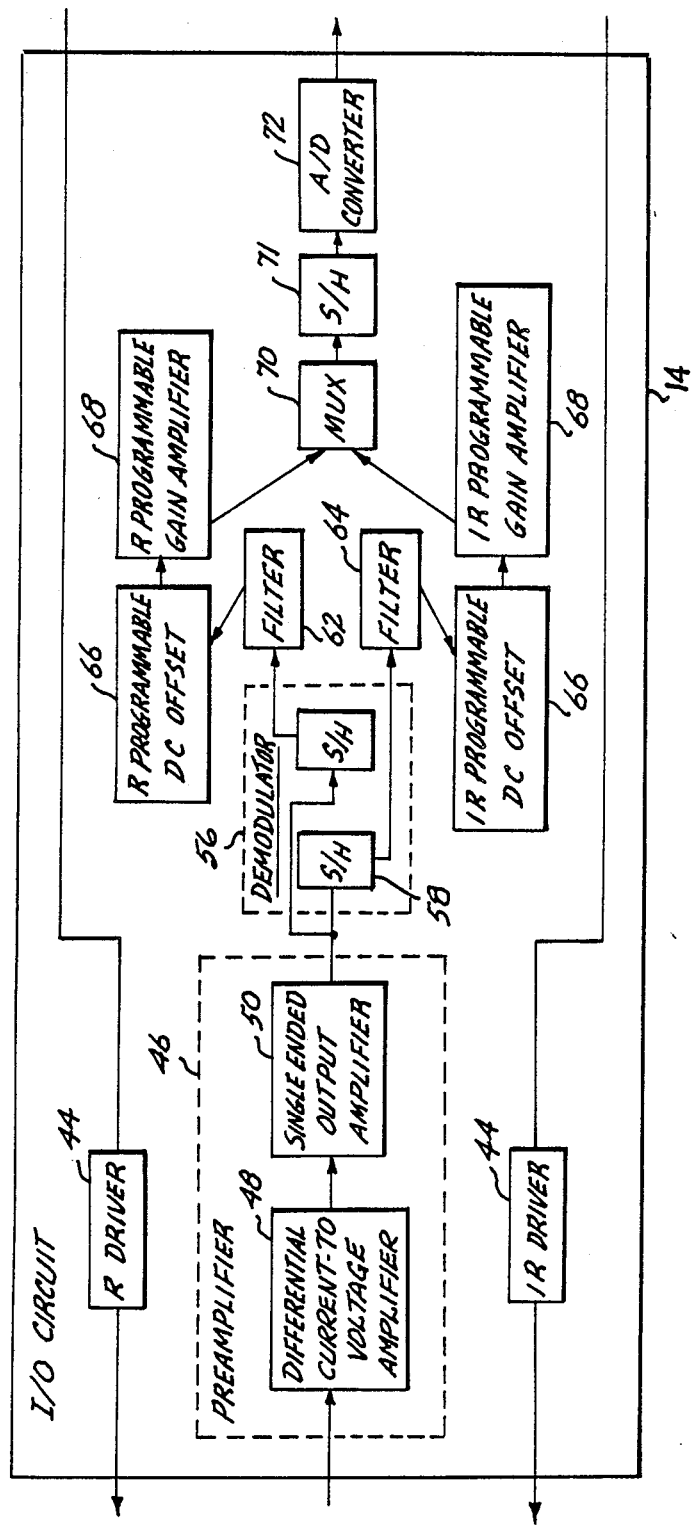
FIG. 11 is a more detailed schematic of the I/O circuit illustrated in the system of FIG. 1.

LEDs 40 and 42 are supplied with current by transistor drivers 44 located in the I/O circuit 14, as shown in FIG. 11. Drivers 44 are controlled by microcomputer 16 to produce current pulses at a 960 Hz repetition rate. The duration of each pulse is 70 microseconds and a pulse is supplied to the red wavelength LED 40 first and then to the infrared wavelength LED 42. The voltage drop across scaling resistors in the drivers 44 allows the magnitude of the current pulses to be determined and, thus, maintained in a manner described in greater detail below. LEDs 40 and 42 respond to the current pulses by producing corresponding light pulses transmitted through the finger to detector 38. Detector 38, in turn, produces a signal that includes information about the pulsatile response of the finger to the red and infrared wavelength light, intermixed at the 960 Hz LED pulse repetition rate.

In a preferred embodiment of the invention, a red optical filter 45 interrupts the lightpath between the LEDs 40 and 42 and the detector 38, as shown in FIG. 8. Preferably, filter 45 is a Kodak No. 29 wratten gel filter. Its function is to eliminate the influence of fluorescent light flicker on the oxygen saturation determination made. As will be appreciated, although the body of sensor 12 may be made of an opaque material that blocks a significant portion of the ambient light, some ambient light may still reach detector 38. Light from the sun and incandescent lamps is substantially continuous. Fluorescent lighting, on the other hand, includes alternating energized and deenergized intervals that form a visually imperceptible flicker. The frequency of the fluorescent light flicker is such that it might influence the signal produced by detector 38 in response to light received from LED 40 at the red wavelength. Thus, the red optical filter 45 is placed over the detector 38 and filters out any fluorescent light present, eliminating the effect its flicker might have on the oxygen saturation determination made.

Figure 12:
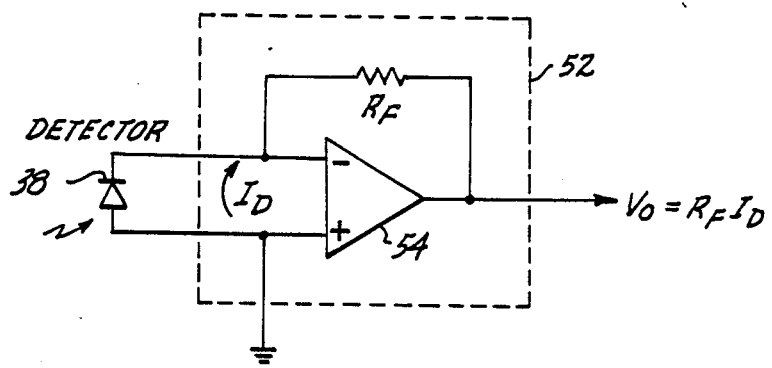
FIG. 12 is a schematic diagram of a conventional current-to-voltage amplifier circuit.

At the I/O circuit 14, the signal from detector 38 is received by a preamplifier 46. In a preferred embodiment, preamplifier 46 includes a differential current-to-voltage amplifier 48 and a single-ended output amplifier 50. To understand the advantages of using the differential amplifier 48, it may first be helpful to consider the operation of a conventional current-to-voltage amplifier as shown in FIG. 12. As shown, a current-to-voltage amplifier 52 is substantially comprised of an operational amplifier 54 and gain determination resistor $R_F$. With a detector 38 connected to the inputs of the amplifier as shown, a current $I_D$ is input to the amplifier upon the detection of suitable wavelength light. The output of amplifier 52 is designated $V_0$ and, as will be appreciated, is equal to the product of the detector current $I_D$ and the gain determination resistor $R_F$. The primary problem with such a construction is that it also amplifies the external interference noise produced, making the signal extracted less accurate.

Figure 13:
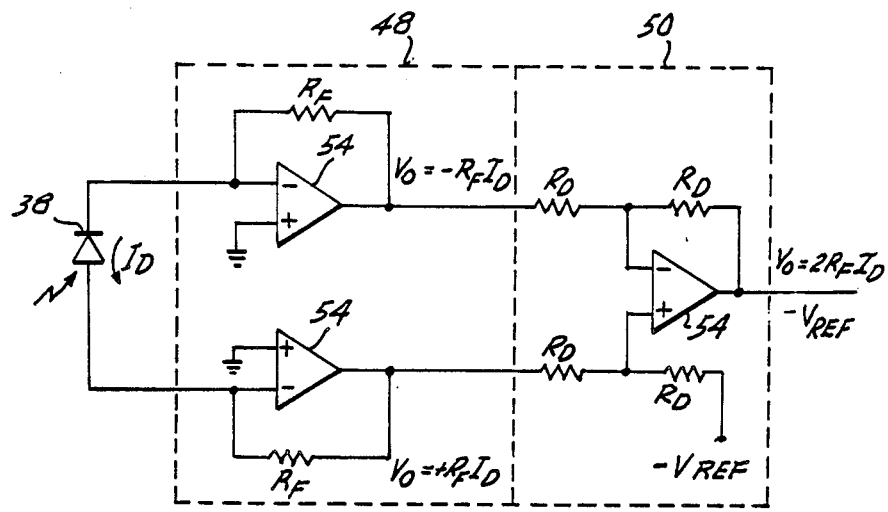
FIG. 13 is a schematic diagram of a differential current-to-voltage preamplifier circuit included in the I/O circuit of FIG. 1.

Adoption of the differential current-to-voltage amplifier 48, when combined with the single-ended output amplifier 50 as shown in FIG. 13, however, eliminates this problem. As shown, the differential amplifier 48 produces positive and negative versions of the output, the absolute value of each version being equal to the product of the gain determination resistance $R_F$ and the detector current $I_D$. These outputs are then supplied to the single-ended output amp 50, which provides unity gain, thus producing an output signal having a magnitude that is twice that of the inputs. An advantage of this arrangement is that external interference noise is cancelled at the single-ended output amplifier 50 by the opposing signs of the two transimpedance amplifier outputs. In addition, twice the signal is produced with the current noise only increasing by a magnitude of 1.414. Therefore, an improved signal-to-noise ratio results.

Figure 10:
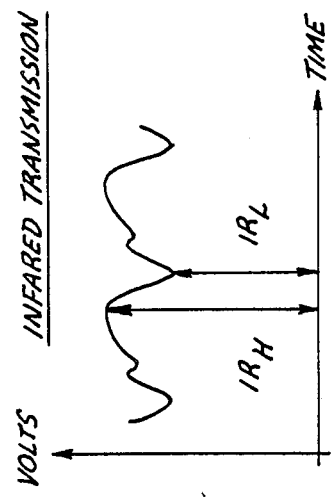
FIG. 10 is a graphical plot as a function of time of the transmission of infrared light through the finger.

At this point, the mixed signal indicative of the red and infrared wavelength responses of detector 38 has been amplified and is input to a demodulator 56 to extract the red pulsatile and infrared pulsatile waveforms shown in FIGS. 9 and 10. In a preferred arrangement, the demodulator 56 includes a sample-and-hold (S/H) circuit 60 that responds to the detector signal produced in response to red wavelength light and a sample-and-hold (S/H) circuit 58 that responds to the infrared wavelength response of detector 38. The timing of circuits 58 and 60 is controlled so that each circuit samples the signal input to demodulator 56 during the portion of the signal corresponding to the wavelength to which it responds. In this manner, two signals are reconstructed from the single input to demodulator 56. As noted above, these signals correspond to the red pulsatile signal and infrared pulsatile signals shown in FIGS. 9 and 10.

To remove high-frequency noise from the outputs of circuits 58 and 60, they are input to lowpass filters 64 and 62. In a preferred embodiment, the "red" lowpass filter 62 and "infrared" lowpass filter 64 each include two stages. The first stage of each filter utilizes a fifth-order, monolithic integrated circuit switched capacitor filter because of its low cost, relatively small physical size and accuracy. Since both the "red" and "infrared" signals pass through nearly identical first-stage filters due to monolithic IC matching, their gain and phase frequency responses are matched. The second stage of each filter is a second-order Bessel filter having a slightly higher roll-off frequency than the first stage. This ensures that the first-stage filter is the dominant filter of the two-stage combination, producing the desired filtering accuracy. The second stage then filters the switching noise from the first-stage output.

The filtered red and infrared pulsatile signals are next prepared for conversion and transmission to the microcomputer 16. As will be discussed in greater detail below, this process involves the use of a programmable DC subtractor or offset 66 followed by a programmable gain amplifier 68 having a gain range from approximately one to 256. The appropriately processed signals are combined at multiplexer 70, sampled and held at 71, and converted to digital form by A/D converter 72 for transmission to microcomputer 16.

Before a more complete discussion of the operation of programmable subtractor 66, programmable gain amplifier 68, multiplexer 70, S/H 71, and A/D converter 72 is provided, several details regarding the signals to be transferred to microcomputer 16 should be noted. For example, as shown in FIGS. 9 and 10, the signal produced by detector 30 in response to light at each wavelength includes components that, for convenience, are termed baseline and pulsatile. The baseline component approximates the intensity of light received at detector 38 when only the "fixed" nonpulsatile absorptive component is present in the finger. This component of the signal is relatively constant over short intervals but does vary with nonpulsatile physiological changes or system changes, such as movement of sensor 12 on the finger. Over a relatively long interval this baseline component may vary significantly. As will be appreciated, the magnitude of the baseline component at a given point in time is substantially equal to the level identified in FIG. 9 as $R_H$. For convenience, however, the baseline component may be thought of as the level indicated by $R_L$, with the pulsatile component varying between the values for $R_H$ and $R_L$ over a given pulse. That pulsatile component is attributable to light transmission changes through the finger resulting from blood volume changes in the finger during a cardiac pulse. Typically, the pulsatile component may be relatively small in comparison to the baseline component and is shown out of proportion in FIGS. 9 and 10.

The determination of $R_{OS}$ in accordance with equation (22) requires accurately measured values for both the baseline and pulsatile signal components. Because the pulsatile components are smaller, however, greater care must be exercised with respect to the measurement of these components. As will be readily appreciated, if the entire signal shown in FIGS. 9 and 10, including the baseline and pulsatile components, was amplified and converted to a digital format for use by microcomputer 16, a great deal of the accuracy of the conversion would be wasted because a substantial portion of the resolution would be used to measure the baseline component. For example, with an A/D converter employed having an input range of between +10 and −10 volts, a signal having a baseline component referenced to −10 volts that is four times that of the pulsatile component can be amplified until the baseline component is represented by a 16-volt difference and the pulsatile signal represented by a 4-volt difference. With a 12-bit A/D converter 72, the total signal can be resolved into 4096 components. Therefore, the number of incremental levels representing the pulsatile signal would be approximately 819. If, on the other hand, the baseline component is removed prior to the conversion, the gained pulsatile signal could be resolved into 4096 intervals, substantially improving accuracy.

Figure 14:
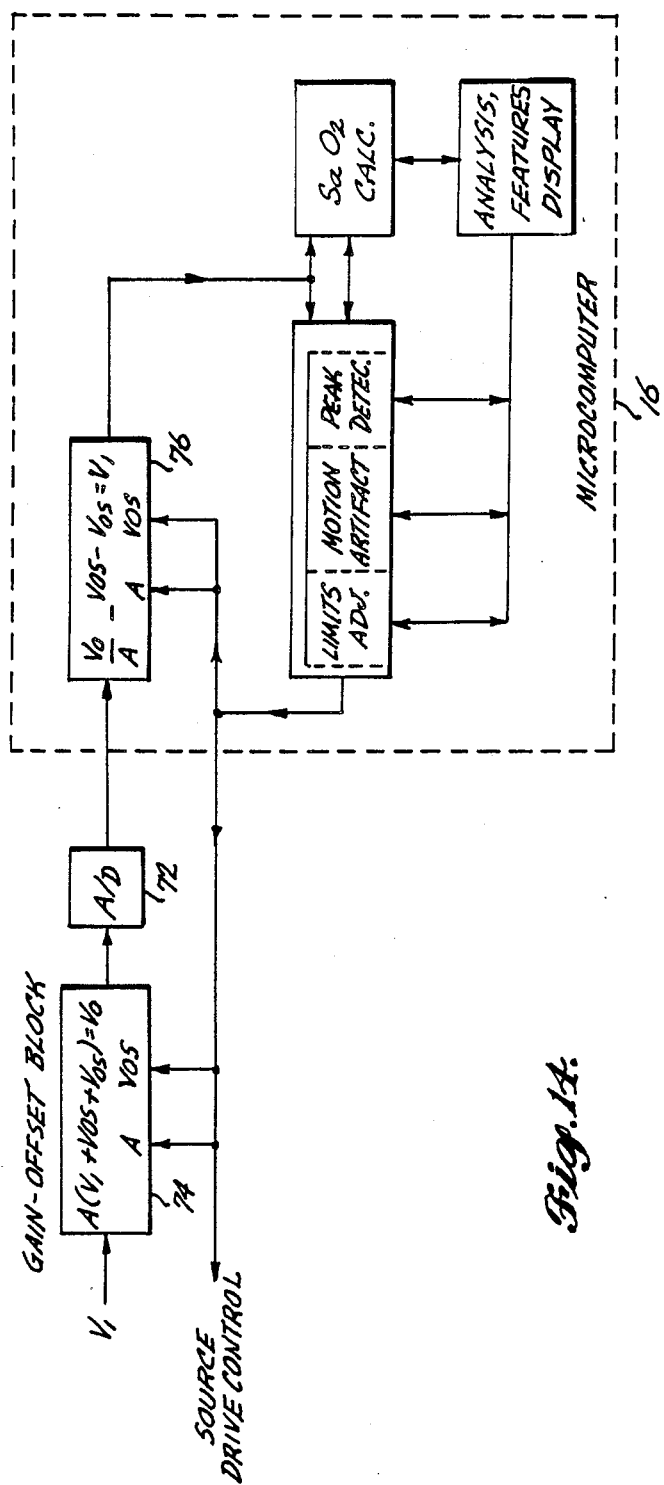
FIG. 14 is a functional block diagram illustrating the basic operation of the feedback control system constructed in accordance with this invention.

The disclosed invention employs this technique, as the first half of a construction-reconstruction process, in the manner schematically outlined in FIG. 14. As shown, an input signal $V_1$ (corresponding to the signals shown in FIGS. 9 and 10) is received from each filter 62 and 64. $V_1$ includes both the baseline and pulsatile components discussed above. As will be described, subsequent operations upon $V_1$ subtract off a substantial "offset voltage" portion of the baseline component, then gain up the remaining substantially pulsatile signal for conversion by A/D converter 72. A digital reconstruction of the original signal is then produced by reversing the process, wherein digitally provided information allows the gain to be removed and the offset voltage added back. This step is necessary because the entire signal, including both the baseline and pulsatile components, is used in the oxygen saturation measurement process.

For purposes of the following discussion, an offset voltage $V_{OS}$ (computed in a manner discussed in greater detail in conjunction with the description of microcomputer software provided below) is defined to be the negative value of the portion of the baseline component to be subtracted. Because some offset error voltage is introduced by the various components of the system, the portion of the signal ultimately attributable to these components $V_{os}$ is also preferably accounted for because it represents an error. As shown in FIG. 14, a signal construction block 74, corresponding to programmable subtractor 66 and programmable amplifier 68, initially processes the input signal $V_1$ by adding to it the negatively defined offset voltage $V_{OS}$. The output of construction block 74, $V_O$, is defined as follows:

$$V_O = (V_1 + V_{OS} + V_{os})A \quad (23)$$

As will be readily appreciated, $V_O$ is substantially proportional to the pulsatile component $V_1$, which contains the pulsatile information desired. Without gain A, this pulsatile signal may be relatively small in comparison to the maximum input range of A/D converter 72. To provide good resolution, therefore, the signal is amplified by gain A, which is sufficient to produce a signal occupying a predetermined portion of the A/D converter 72 input range. In this manner, the resolution of the digital conversion is improved by providing a large pulsatile signal for measurement.

If $R_H$, $R_L$, $IR_H$ and $IR_L$, as discussed previously, are to be measured and the oxygen saturation determined, however, the foregoing process must be reversed. As will be appreciated, dividing both sides of the equation (23) by the gain A produces:

$$V_1 + V_{OS} + V_{os} = V_0/A \quad (24)$$

Restructuring of equation (24) results in:

$$V_1 = V_0/A - V_{OS} - V_{os} \quad (25)$$

Thus, the original input signal $V_1$ containing the baseline and pulsatile components can be reconstructed at block 76 by dividing the output of the A/D converter 72, $V_0$, by the gain A and the subtracting the offset voltages $V_{OS}$ and $V_{os}$. The reconstruction is preferably performed at microcomputer 16 before oxygen saturation computations are initiated, allowing measurements based on the full signal to be performed. As will be appreciated, to accomplish this, values for $V_{OS}$, $V_{os}$ and A must be supplied to microcomputer 16.

Feedback from microcomputer 16 is also required to maintain the values for $V_{OS}$, $V_{os}$ and gain A at levels appropriate to produce optimal A/D converter 72 resolution. Likewise, as shown in the FIG. 14, feedback to the source drivers 44 may be used to help optimize the conversion. Proper control requires that the microcomputer continually analyze, and respond to, the offset voltages $V_{OS}$ and $V_{os}$, gain A, driver currents $I_0$ and the output of A/D converter in a manner to be described next.

Briefly, with reference to FIG. 15, thresholds L1 and L2 slightly below and above the maximum positive and negative excursions L3 and L4 allowable for the A/D converter 72 input are established and monitored by microcomputer 16 at the A/D converter output. When the magnitude of the signal input to, and output from, A/D converter 72 exceeds either of the thresholds L1 or L2, the drive currents $I_D$ are readjusted to increase or decrease the intensity of light impinging upon the detector 38. In this manner, the A/D converter 72 is not overdriven and the margin between L1 and L3 and between L2 and L4 helps assure this even for rapidly varying signals. An operable voltage margin for A/D converter 72 exists outside of the thresholds, allowing A/D converter 72 to continue operating while the appropriate feedback adjustments to A and $V_{OS}$ are made.

When the signal from A/D converter 72 exceeds positive and negative thresholds L5 or L6, microcomputer 16 responds by signaling the programmable subtractor 66 to increase or decrease the voltage $V_{OS}$ being subtracted. This is done through the formation and transmission of an offset code whose magnitude is dependent upon the level of the signal received from converter 72.

The manner in which the various thresholds are established and the relationship of the offset codes to the signal received can be altered to produce substantially any form of control desired. In addition, gain control codes could be established by microcomputer 16 in response to the output of A/D converter 72 to vary the gain of amplifier 68 as a function of converter output. Thus, the arrangement shown in FIG. 15 is illustrative only and represents the currently preferred embodiment. This embodiment of the construction-reconstruction process will now be discussed in greater detail in conjunction with a portion of the oximeter software stored in the erasable, programmable read-only memory (EPROM) 78 of microcomputer 16. The software defines a program of instructions to be executed by the central processing unit (CPU) 80 of microcomputer 16 and governs the manner in which microcomputer 16 provides servosensor control as well as produces measurement outputs of display.

Figure 16:
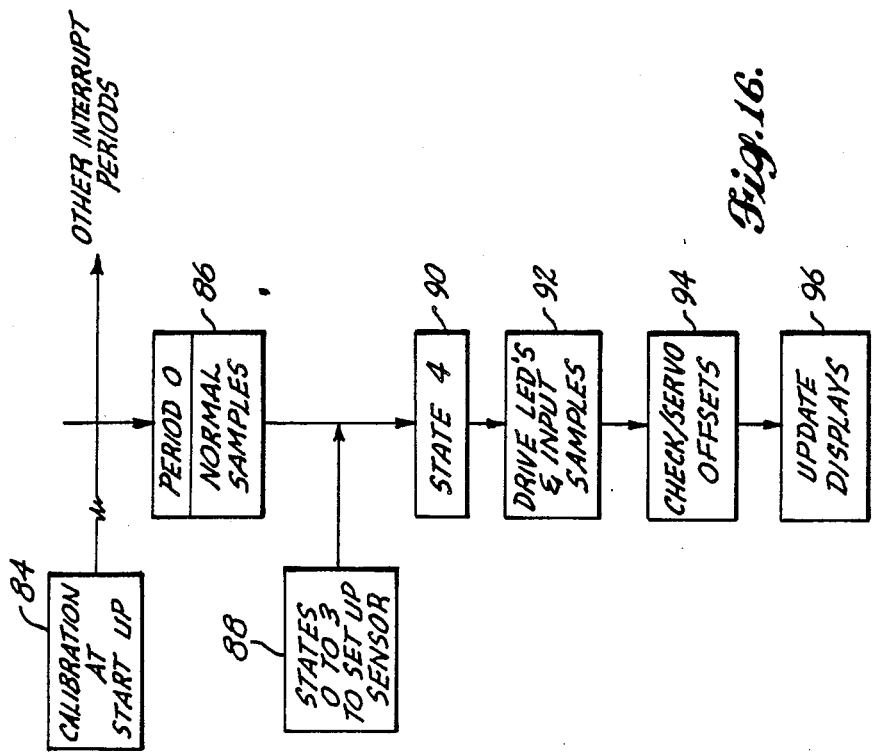
FIG. 16 is a block diagram of a portion of an interrupt level software routine included in the microcomputer illustrated in FIG. 1.

The first segment of the software to be considered is an interrupt level routine 82, shown in part in FIG. 16. Interrupts are events generated by a programmable timer, which is included in CPU 80 and is initialized at the power-up of microcomputer 16. An interrupt event "interrupts" the part of the program currently being executed by CPU 80 and transfers control to a new instruction sequence associated with the particular interrupt. When processing associated with the interrupt is completed, the program may be resumed at the point of interruption, or elsewhere, depending on any status changes that may have resulted from processing of the interrupt.

Normal interrupt processing in accordance with routine 82 begins once CPU 80 has completed a number of preliminary routines, including power-up reset, calibration, and miscellaneous test code routines. Microcomputer 16 and the software stored in EPROM 78 are organized to provide real-time processing at the interrupt level routine 82, as well as at the other, prioritized task levels noted below. Processing at the various task levels is prioritized such that the highest priority task ready and waiting to run is given control, in the absence of an interrupt. Thus, a task may be interrupted to execute a higher priority task and then resumed when processing at the higher priority level is completed. Interrupt processing occurs at a priority level above all other tasks.

While the interrupt routine 82 employed may have a number of subroutines controlling various portions of oximeter 10 operation, such as the filtering performed by lowpass filters 62 and 64, only the details of the interrupt period subroutine directly pertinent to servosensor control are shown in FIG. 16.

As shown at block 84, processing of the interrupt level routine 82 does not begin until calibration is complete. After calibration, a nominal interrupt period zero subroutine 86 may be reached. This subroutine is responsible for normal sampling and includes five states, zero through four. Briefly, at block 88, a sensor set-up subroutine is represented as including states zero to three of the period zero subroutine 86. As will be discussed in greater detail below, during these states sensor parameters including amplifier gain A and offset voltages $V_{OS}$ are initialized, provided that a finger is present in the sensor. State four of the interrupt period zero subroutine 86 is the normal data acquisition state and is shown at block 90. This state is reached when, for example, a finger is present in sensor 12, the amplifier gain, offset voltages, and driver currents are within their appropriate ranges, and the software is not performing a test task. As shown in FIG. 16, state four of the period zero subroutine 86 includes a number of instructions. At block 92 drive currents are applied to LEDs 40 and 42 and the resulting signal produced by detector 38 is sampled. The signals produced in response to light at each wavelength are then compared against the desired operating ranges to determine whether modifications of the driver currents and voltage offsets are required. This step is shown at block 94. The exact manner in which these control variables are tested and modified is discussed above and in greater detail below. Finally, as shown in block 96, state four of the period zero subroutine 86 updates the displays 20 of oximeter 10.

Figure 17:
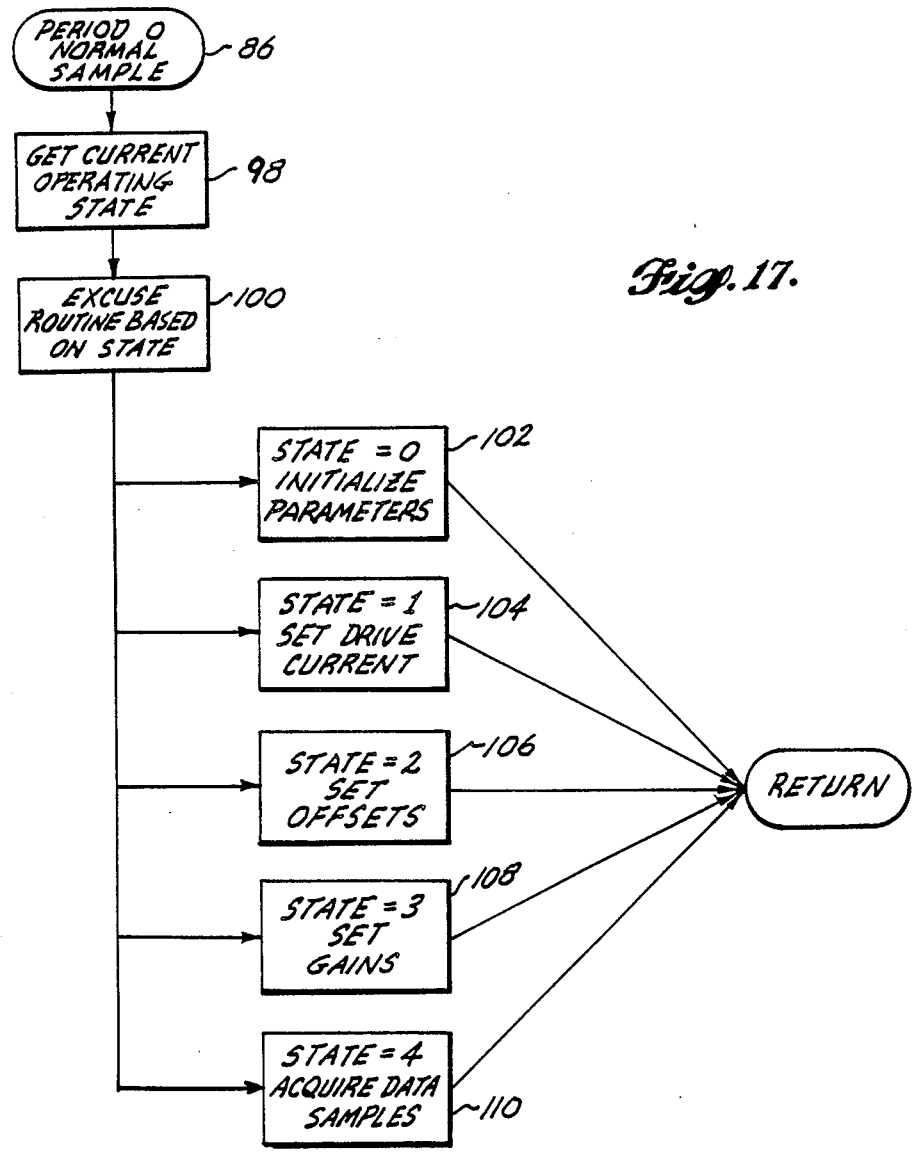
FIGS. 17 through 20 are more detailed block diagrams of the interrupt level routine depicted in FIG. 16.
Figure 18:
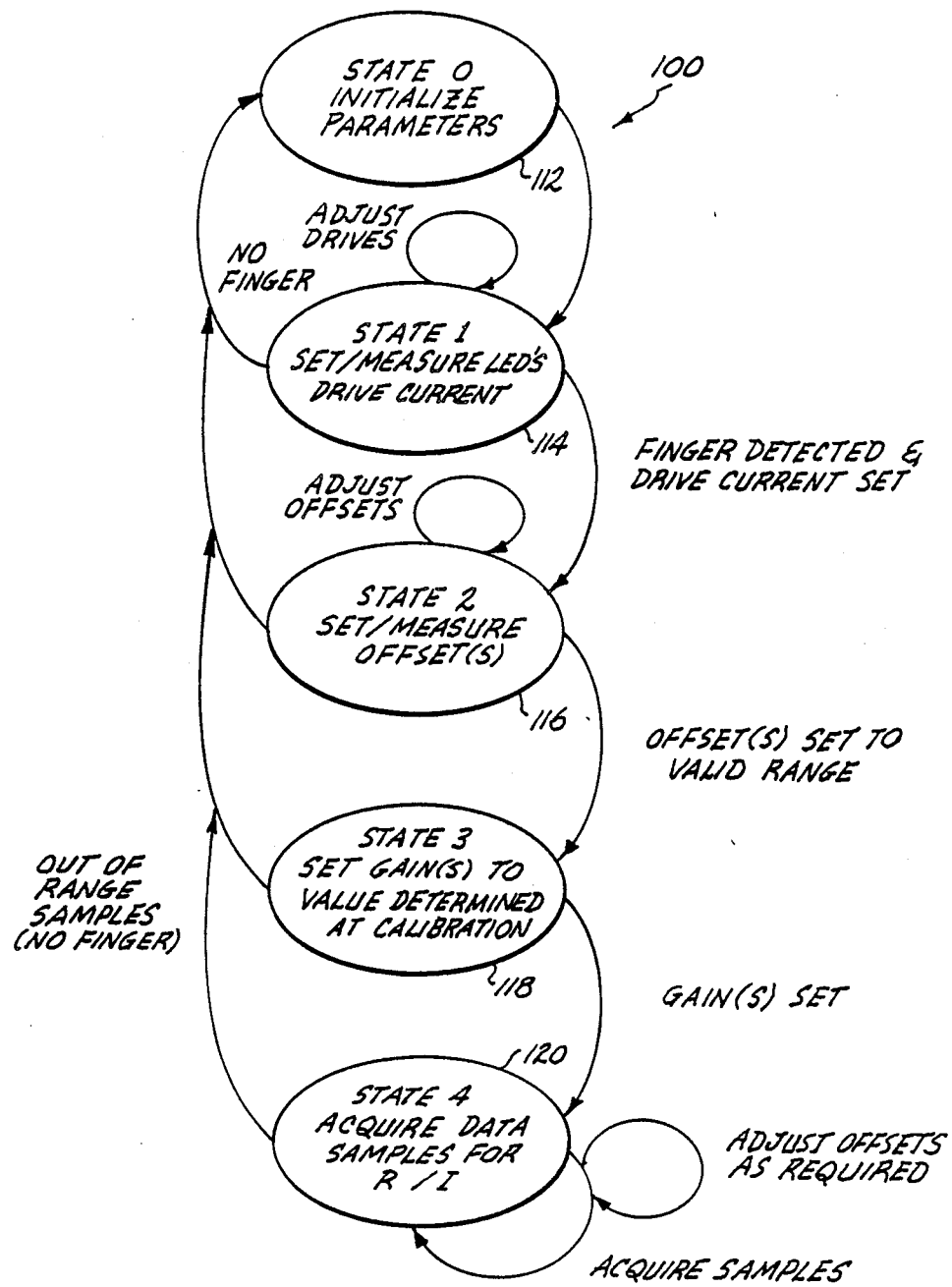

The operation of the period zero subroutine 86 of the interrupt routine 82 is now discussed in greater detail in conjunction with FIG. 17. As shown at block 98, the current state of sensor set-up is determined, including the levels of LED drive current, amplifier gain, and offset voltages. At block 100, these sensor set-up states are analyzed to determine which of the five period zero interrupt state subroutines, indicated by blocks 102, 104, 106, 108, and 110, are to be executed. The manner in which the various state subroutines are sequenced for execution by block 100 is shown in greater detail in FIG. 18. Generally, states are entered in ascending order. Thus, the state zero subroutine 102 forms an initial block 112 in the sequencing performed by block 100. In this state, as noted above and discussed in greater detail below, the various parameters and variables employed by oximeter 10 are initialized. As shown, the sequential processing returns to state zero whenever the conditions required for a particular state routine are violated. Given the general processing of state routines in ascending order, with the parameters initialized at block 112, the state one subroutine 104 is reached at block 114. This routine sets the drive currents applied to LEDs 40 and 42. The state one subroutine 104 is maintained until the drive currents are set, at which time sequential processing moves to the state two subroutine 106 shown at block 116. In the event that the state one subroutine 104 determines that the LED drive currents cannot be set, processing is returned to the state zero subroutine at block 112.

Once the state two subroutine 106 of the interrupt period zero subroutine 86 is reached at block 116, the offset voltages are adjusted. The state two subroutine 106 is maintained until the offsets are properly adjusted or it is determined that they cannot be so adjusted given the current drive settings. With the offsets properly adjusted, sequential processing continues to the state three subroutine at block 118. If they cannot be properly adjusted, however, the interrupt period zero subroutine 86 is reset to state zero.

The amplifier gain levels determined during calibration are set in the state three subroutine shown at block 118. Once properly set, sequencing continues to the state four subroutine at block 120, where the normal analog signal processing is performed.

Figure 19:
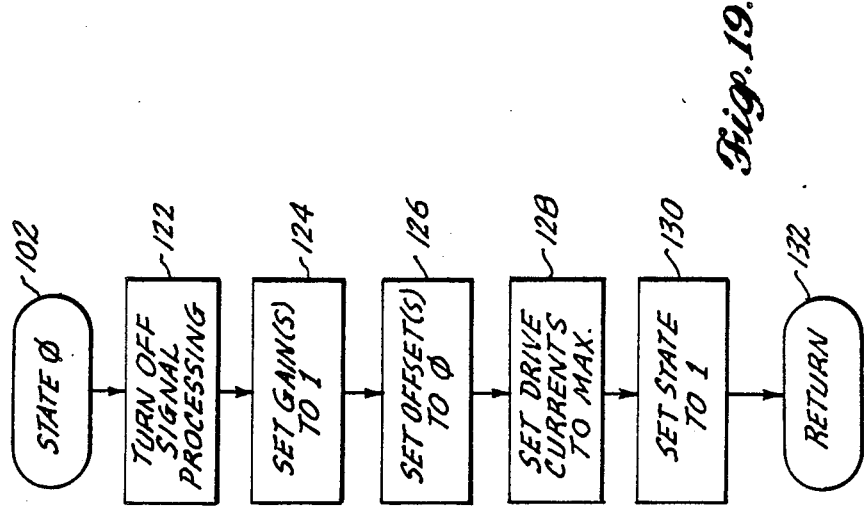

With this basic understanding of the various states of the period zero normal sample subroutine 86 and the sequential order in which those states are processed, a more detailed discussion of the various states of the period zero subroutine is now provided. FIG. 19 is a detailed flow chart of the processing included in the state zero subroutine 102 of FIG. 17. As shown in block 122, the first instruction in the state zero subroutine 102 calls for normal signal processing to be halted. At block 124, the gain for each channel is reset to one and the offset voltage for each channel is reset to zero at block 126. Similarly, the LED drive currents for each channel are initialized to their maximum values at block 128. With these conditions performed, the sequential processing of the various state routines of the period zero interrupt subroutine 86 cause the state one subroutine 104 to be reached at block 130. A return is provided at block 132 and the processing associated with the state one subroutine will occur at the time of the next period zero interrupt.

Figure 20:
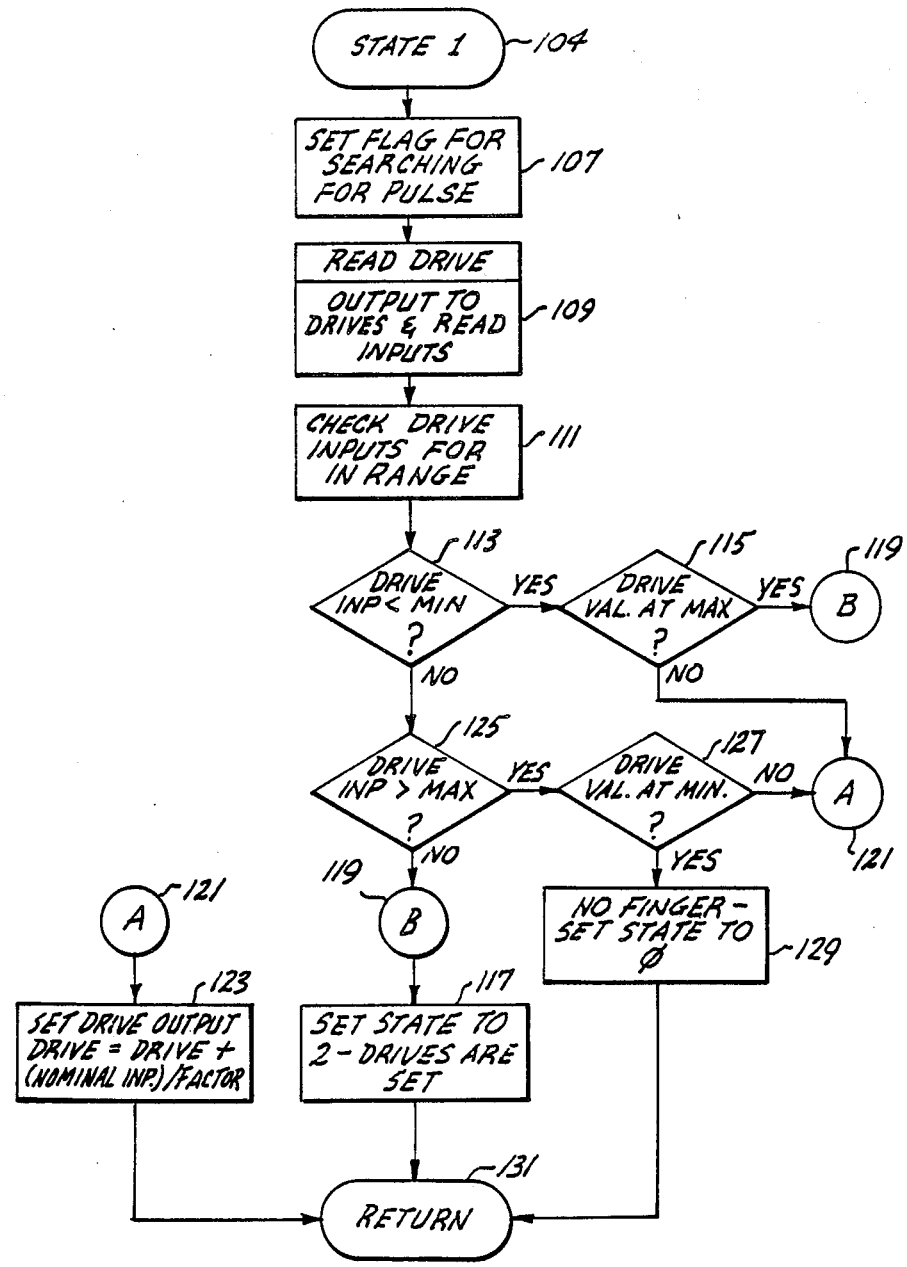

The state one subroutine 104 of FIG. 17 is shown in greater detail in FIG. 20. When the state one subroutine 104 is executed, a pulse search flag is set at block 107 to indicate that no pulse is available. At block 109, the presently established drive currents are output to LEDs 40 and 42 and the resulting signals produced from detector 38 are read. The signals input to the drivers 44 are then checked to determine whether they are in a valid operating range at block 111. More particularly, a test is performed at block 113 to determine whether the driver inputs are below some predetermined acceptable minimum value. If either input is below the acceptable minimum, the output of the corresponding driver 44 is then tested at block 115 to determine whether it is at some predetermined maximum value. With the output at a maximum, it is assumed that no greater drive current can be provided and the interrupt period zero subroutine 86 is advanced to state two at block 117 via block 119.

If, on the other hand, the input to either driver 44 is determined to be less than the predetermined minimum at block 113, but block 115 indicates that the drive current is not at its maximum value, the routine progresses via block 121 to block 123 where the drive is increased in proportion to the drive current read. In this manner, an attempt is made to adjust the drive current to a nominally desired level. More particularly, the input to driver 44 is increased by an amount equal to some nominal value minus the present input, all divided by a predetermined constant. The validity of the drive setting is then checked the next time that interrupt period zero routine 86 is performed.

If block 113 determines, for each channel, that the input to driver 44 is not below the predetermined minimum, a test is performed at block 125 to determine whether the input is above some predetermined maximum. If an input signal is above the desired range, the output of the corresponding driver 44 is checked at block 127 to determine whether it is at some predetermined minimum value. A driver output at its minimum value is interpreted at block 129 to indicate that no finger is present in the sensor and the routine is returned to state zero. If, on the other hand, block 127 indicates that the output of driver 44 is not at its minimum value, block 123 is reached via block 121, allowing the drive output to be adjusted in an attempt to bring the drive input back below the maximum predetermined value exceeded at block 125. More particularly, the drive output is adjusted at block 123 by decreasing the input to driver 44 by an amount equal to a nominal input minus the present input divided by some predetermined factor.

Finally, if the driver input falls within a predetermined desired operating range, the tests at block 113 and 125 will both be failed and the subroutine will progress to block 117 via block 119. This indicates that the drives are properly set and block 117 allows the subroutine to progress to state two at the next period zero interrupt via block 131. Although not shown in FIG. 20, such valid drive input values must exist multiple concurrent times before the state two subroutine 106 is reached.

Figure 21:
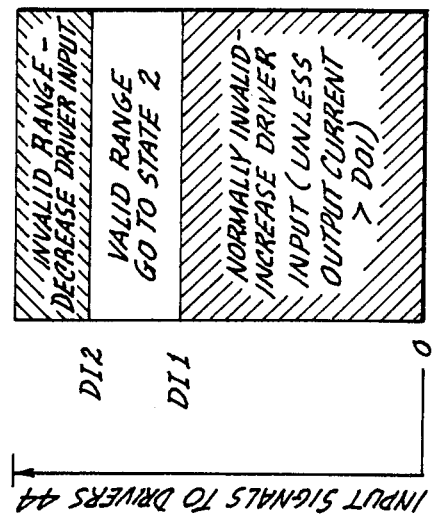
FIG. 21 is a graphical representation of the possible ranges of current supplied to the sensor, showing the desired response of the I/O circuit and microcomputer at each of the various possible ranges as a function of sensor output.

FIG. 21 is a pictorial illustration of the response of the state one subroutine 104 to the various input and output levels of the drivers 44. As shown, if the input current to driver 44 is below a predetermined minimum, DI1, an invalid condition is indicated unless the output current of driver 44 is greater than some predetermined maximum DO1. If DO1 is not exceeded, the driver inputs are adjusted upward before the state two subroutine 106 is reached. Similarly, if the input signal to drivers 44 exceeds some predetermined maximum DI2, an invalid condition is indicated and the input to the drive is adjusted downward. When the input signal to drivers 44 falls between the levels DI1 and DI2, however, the signal is within a valid range and the state two subroutine 106 is directly accessed.

Figure 22:
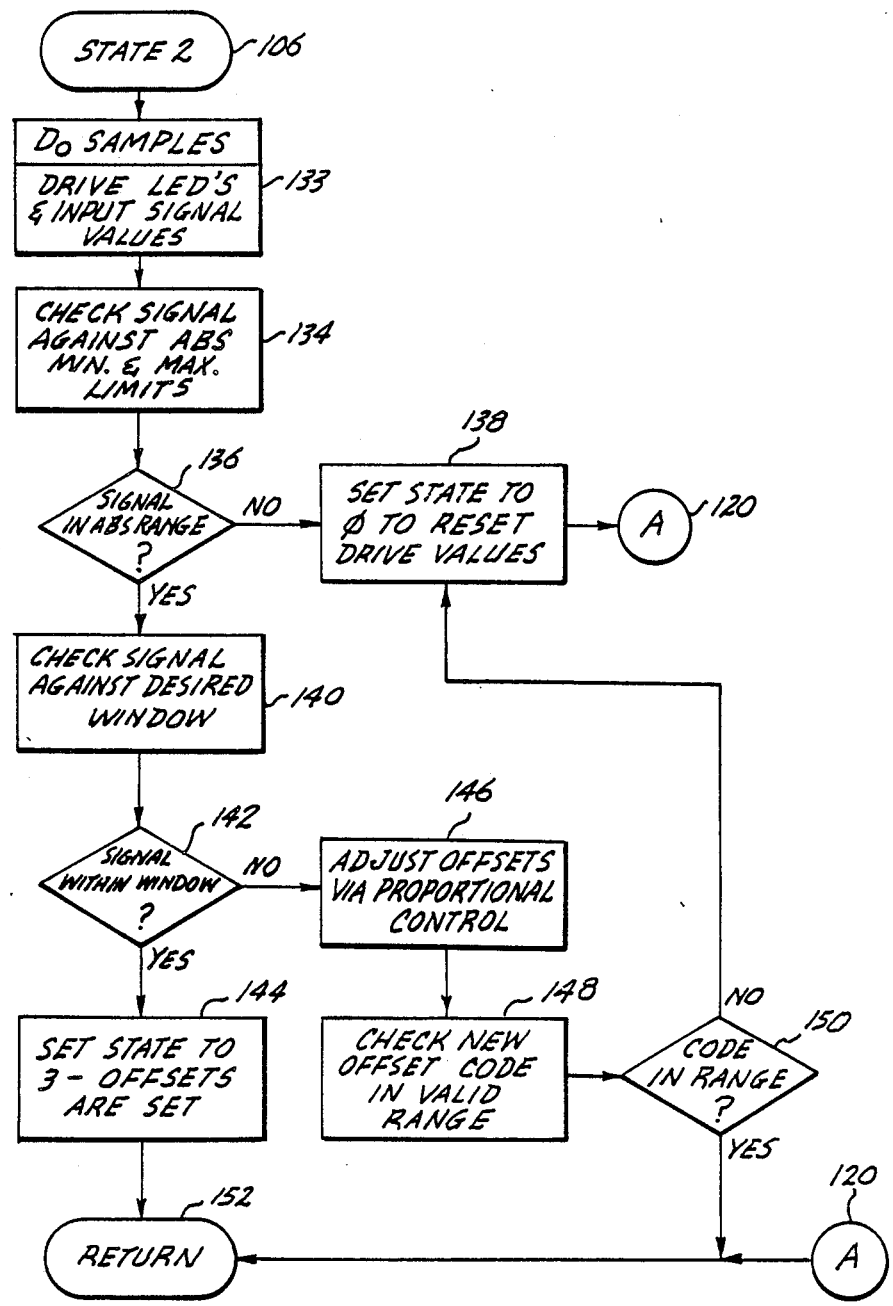
FIGS. 22 through 24 are further detailed block diagrams of the interrupt level routine depicted in FIG. 16.

FIG. 22 is a more detailed flow chart of the state two routine 106 of the period zero interrupt subroutine 86. As shown, at step 133, the drive currents previously established at the state one subroutine 104 are provided to LEDs 40 and 42 and the response of detector 38 as processed by I/O circuit 14 is read. Thus, a signal is received corresponding to each wavelength of light and the signals of both channels are processed in the following manner. At block 134, the signal at each channel is checked to determine whether it is within an absolute range extending between limits L1 and L2 as shown in FIG. 15. As indicated at block 136, if the signal is outside this predetermined range, the state is reset to zero at step 138 and the input signal to drivers 44 is adjusted in the manner described above to produce an acceptable drive current for LEDs 40 and 42.

When the test performed at block 136 indicates that the signals from A/D converter 72 are within the range between L1 and L2, the state two subroutine 106 progresses to block 140. There, the signal for each channel is checked against a window defined between an upper limit L5 and a lower limit L6. If the signal falls within those limits, block 142 of the subroutine causes the program to be advanced to state three of the period zero interrupt subroutine 86 at block 144 without further adjustments being made. This indicates that the offset voltages are properly set. If, on the other hand, block 142 indicates that the signal is not within the window defined between L5 and L6, block 146 adjusts the offset voltage employed by subtractor 66 in proportion to the level of the signal received. For example, the offset may be either increased or decreased by an amount equal to the signal level divided by some predetermined factor. The adjustment of the offset voltage is accomplished by establishing a new offset code to be transmitted to subtractor 66. This new code is checked at block 148 to determine whether it is within a range of valid codes. The test is performed at block 150 and if the new code is not valid, the state is reset to zero via block 138 so that the drive currents for LEDs 40 and 42 can be reinitialized. If the code is in range, a return is accessed at block 152.

Figure 23:
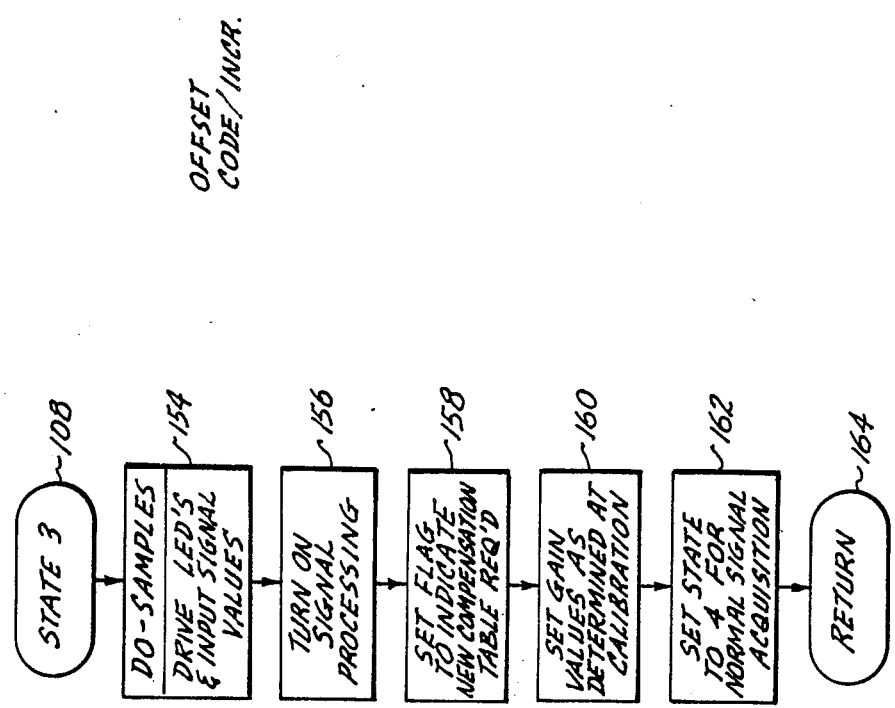

The operation of the state three subroutine 108 of the period zero interrupt subroutine 86 is shown in greater detail in FIG. 23. At block 154, the present drive current signals are provided to drivers 44 to drive LEDs 40 and 42. No samples of the input channels from I/O circuit 14 are made in this state. At block 156, a flag is set to initiate signal processing. In addition, a flag is set at step 158 to cause the generation of an appropriate independently derived calibration curve based upon information received from sensor 12. A gain code established during calibration is then set at block 160 to determine the gain of amplifier 68 and the period zero interrupt routine 86 is progressed to the state four subroutine 110 at block 162 via return 164.

Figure 24:
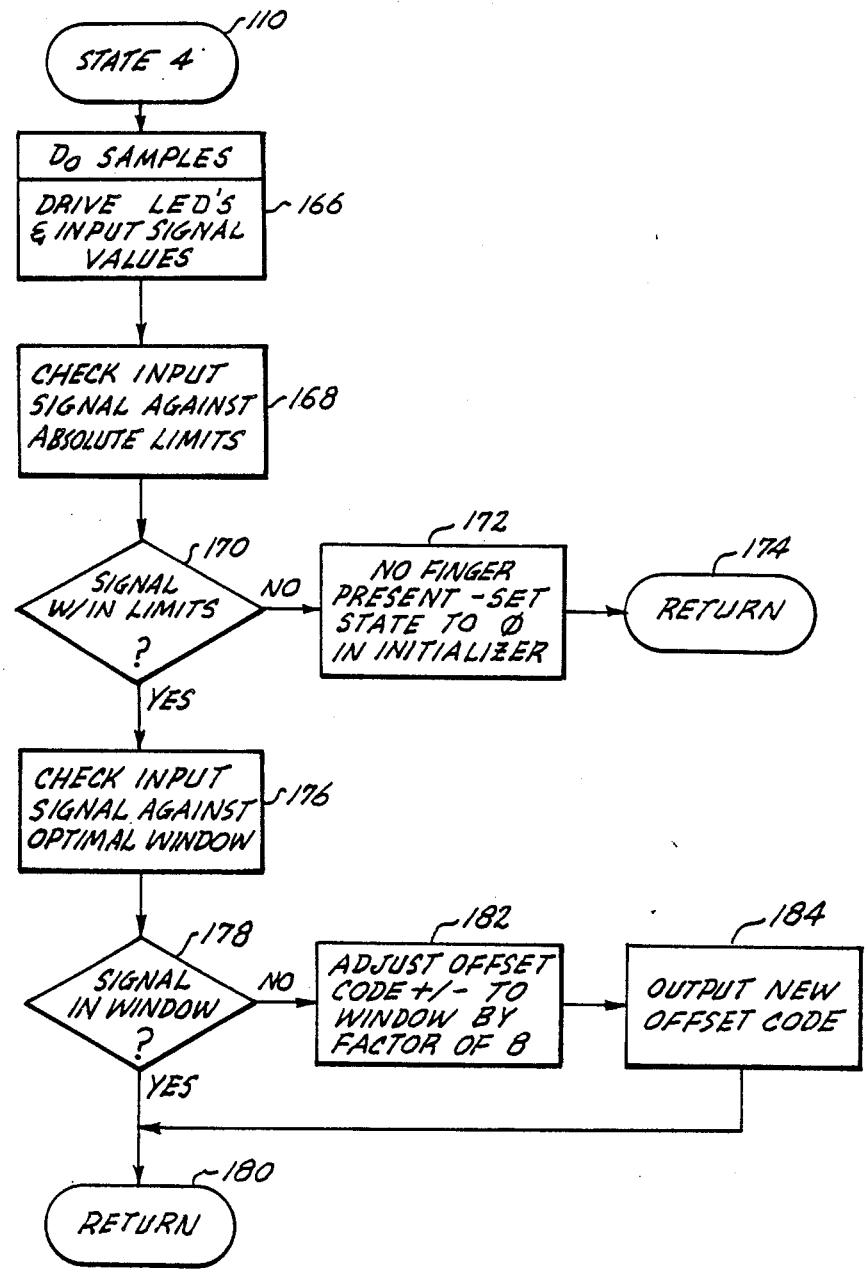

The details of the state four subroutine 110 are shown in FIG. 24. Processing begins with the output of signals to drivers 44 for the production of drive currents at LEDs 40 and 42. Signals from each channel as processed by the subtractor 66 and amplifier 68 are then sampled and stored at block 166. These samples are then checked at block 168 against the maximum and minimum range limits L3 and L4 shown in FIG. 15. If the signal is not within those limits, block 170 causes the subroutine to progress to block 172 where an indication is produced that a finger is no longer present in sensor 12 and the state is reset to zero via step 174.

Figure 15:
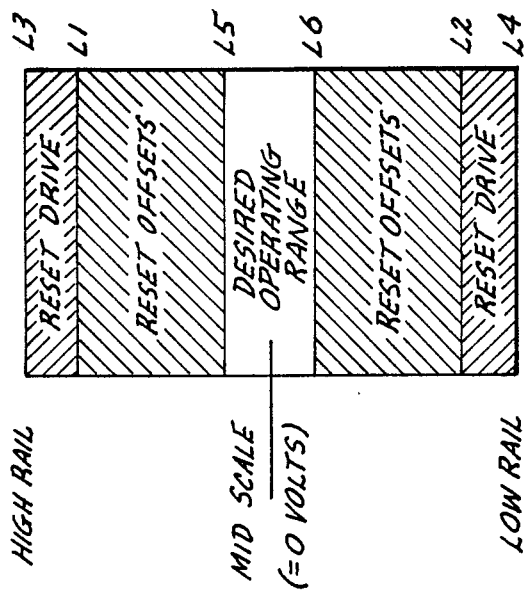
FIG. 15 is a graphical representation of the possible ranges of I/O circuit output, showing the desired responseto the I/O ciruit and microcomputer at each of the various possible ranges.

If, on the other hand, the signal is within the absolute maximum range, the samples are again checked at block 176 to determine whether they are within the desired operating range, shown in FIG. 15 as lying between limits L5 and L6. If they are, block 178 directs the program to a return at block 180. This indicates that the samples received are acceptable and allows computational software to produce a value of $R_{OS}$. If block 178 indicates that the signal is not within the desired operating range, however, the program is directed to step 182 where the offset voltage is adjusted upward or downward by a factor of eight to bring it within the desired range. At block 184, the code for this new offset voltage is output.

Figure 25:
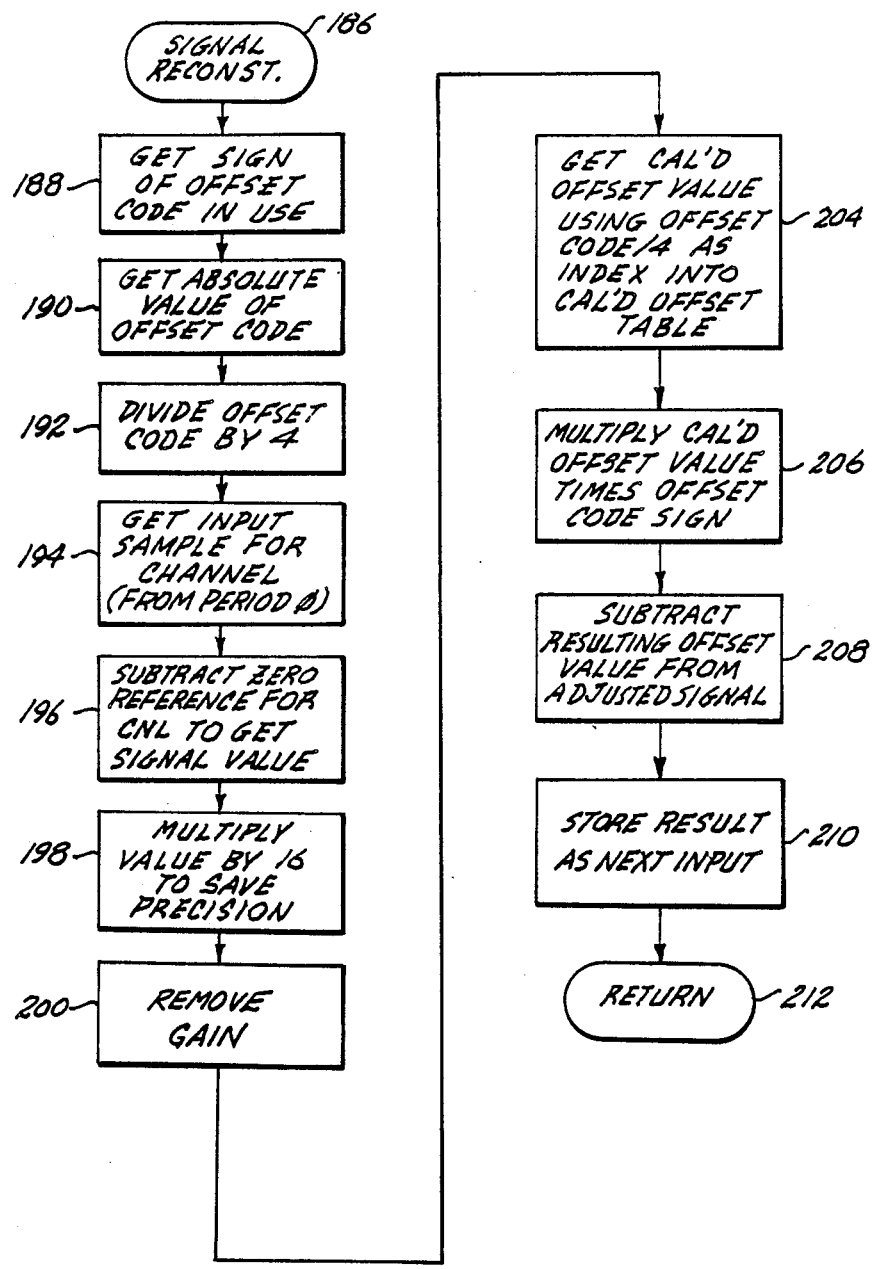
FIG. 25 is a block diagram of reconstruction software included in the microcomputer illustrated in FIG. 1.
Figure 27:
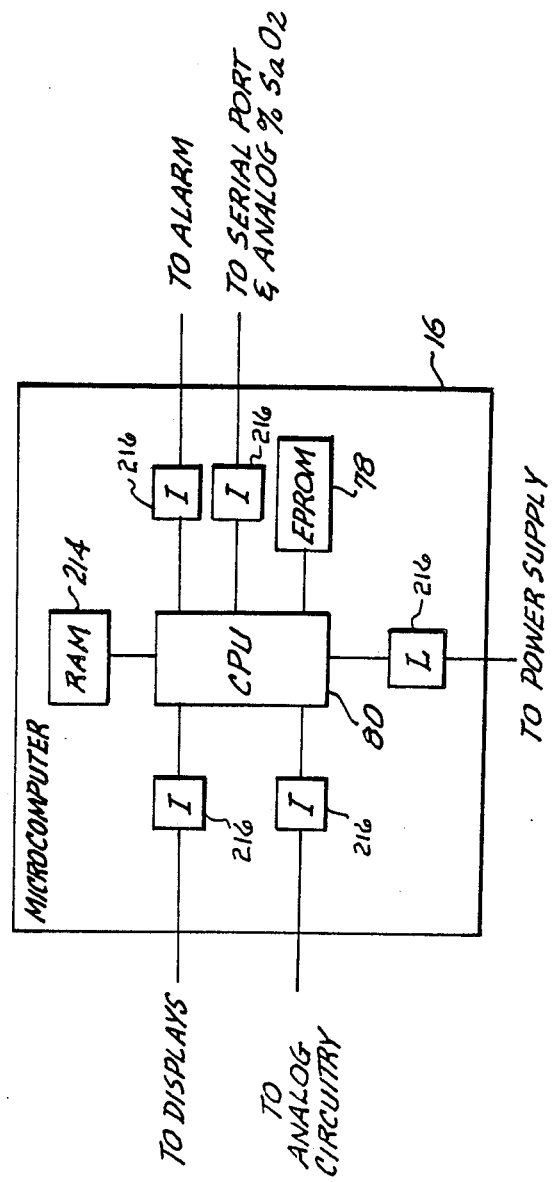
FIG. 27 is a more complete schematic diagram of the microcomputer illustrated in FIG. 1.

As noted previously, before the signal samples produced in the state four subroutine 110 can be used in computations, they must be converted back to valid signals that do not include the effects of gain and offset. The instructions 186 for this reconstruction process are shown in FIG. 25. This routine is executed during an interrupt event period not shown in FIG. 16. Signal reconstruction is performed for each channel and begins at a first block 188 where the sign of the offset code currently in use is determined. Then, at block 190, the absolute value of the offset code is extracted and divided by four at block 192. This divided offset code is used as an index for a calibrated offset table shown in FIG. 26. This table is generated during calibration and contains the calibrated offset voltage corresponding to each offset code.

From block 192, the signal reconstruction routine 186 progresses to block 194 where the present signal sample for the channel involved, as produced by the period zero interrupt subroutine 86, is retrieved. At block 196, the equivalent zero reference value, determined at calibration, is subtracted from the input sample to produce a signed value. To allow subsequent arithmetic operations to be performed with the retention of a greater number of bits, the 12-bit input signal is scaled to a 16-bit number at block 198.

At block 200, the gain previously applied to the signal by amplifier 68 is removed. The effect of the offset voltages is then removed from the signal in the following manner. The calibrated offset value equivalent to the offset code is extracted from the table shown in FIG. 26 at block 204. This calibrated offset value is converted to its signed equivalent at block 206 and is subtracted from the previously processed signal at block 208. This value is then stored at block 210 for subsequent processing accomplished via a return at block 212.

In addition to the analog sample processing task discussed above, the software may include a time task, display drive task, keyboard operation task and test routine task. The analog sample processing task has the highest priority of these various tasks.

As noted, the instructions for the software that controls the signal construction-reconstruction process discussed above are stored in EPROM 78 of microputer 16. Simlarly, values for $R_H$, $R_L$, $IR_H$, $IR_L$, and signal period are determined pursuant to peak-detection software contained in EPROM 78. These values are stored in random-access memory (RAM) 214 for operation upon by CPU 80 in accordance with further computational instructions stored in EPROM 78. Interfaces 216 act as input and output buffers for microcomputer 16.

The computational software in EPROM 78 initially causes CPU 80 to determine the present value for $R_{OS}$ by substituting the measured values for $R_H$, $R_L$, $IR_H$, and $IR_L$ into equation (22):

$$R_{OS} = \frac{\ln(R_L/R_H)}{\ln(IR_L/IR_H)} \tag{26}$$

Then, the computational software instructs CPU 80 to determine the oxygen saturation from $R_{OS}$ by use of a calibration curve, such as the one depicted in FIG. 7. The calibration curve is a plot of the relationship between independently determined oxygen saturations corresponding to values of $R_{OS}$ produced by oximeter 10 in accordance with the technique described above.

With sufficiently large space in EPROM 78, enough points along the calibration curve can be stored in a look-up table to allow CPU 80 to extract an accuate indication of oxygen saturation from the value of $R_{OS}$ input to EPROM 78. The storage of a sufficient number of calibration curve data points may, however, necessitate the use of an undesirably large-capacity EPROM 78. For that reason, a second method of storing the calibration curve information is preferred.

Pursuant to that method, once independently derived data associating $R_{OS}$ with the oxygen saturation is obtained, a mathematical expression between the two can be derived from a plot of the curve. The basic formula and the coefficients of the formula's variables are then stored in EPROM 78. When a value for $R_{OS}$ is measured, CPU 80 extracts the coefficients from EPROM 78 and computes a value for the oxygen saturation. This technique allows information completely identifying the entire calibration curve, or a family of such curves, to be stored within a relatively small amount of EPROM 78 space.

The computational software in EPROM 78 also instructs CPU 80 to determine the pulse rate from the signal period. Displays 20 then provide visible and audible outputs of the oxygen saturation and pulse rate in a manner conveniently used by the operator of oximeter 10.

While the references have been described with reference to a preferred embodiment, it is to be clearly understood by those skilled in the art that the invention is not limited thereto, and that the scope of the invention is to be interpreted only in conjunction with the following claims.

The embodiments of the invention in which an exclusive property or privilege is claimed are defined as follows:

1. An apparatus for receiving and processing signals, produced by a sensor, that contain information about the oxygen saturation of arterial blood flowing in tissue, said apparatus comprising:
    offset subtraction means for subtracting from said sensor signal a controlled portion of said signal, said offset subtraction means having an output that is substantially equal to the portion of said sensor signal remaining after said controlled portion is subtracted therefrom;
    control means for receiving said output of said offset subtraction means and providing a subtraction control signal, which is dependent on said output, to said subtraction means to control the magnitude of said portion of said sensor signal; and analyzing means for receiving said output of said subtraction means and said controlled portion of said signal and producing an indication of the oxygen saturation of said arterial blood flowing in said tissue.

2. The apparatus of claim 1, wherein said subtraction means subtracts the same said portion from said sensor signal when said subtraction means output is within a first predetermined range.

3. The apparatus of claim 2, wherein said subtraction means subtracts an adjusted said portion from said sensor signal when said subtraction means output falls within a second predetermined range, said magnitude of said adjusted portion being a function of the magnitude of said subtraction means output.

4. An apparatus for receiving and processing signals, produced by a sensor, that contain information about the oxygen saturation of arterial blood flowing in tissue, said signals including a relatively periodic pulsatile component superimposed upon a slowly varying baseline component, said apparatus comprising:

offset subtraction means for subtracting from said sensor signal a controlled portion of said signal, said offset subtraction means having an output that roughly approximates said periodic pulsatile component;

control means for receiving said output of said offset subtraction means and providing a subtraction control signal, which is dependent on said output, to said subtraction means to maintain the magnitude of said controlled portion of said sensor signal roughly approximate to said baseline component; and analyzing means for receiving said output of said subtraction means and producing an indication of the oxygen saturation of said arterial blood flowing in said tissue.

5. The apparatus of claim 4, wherein said subtraction means subtracts the same said portion from said sensor signal when said subtraction means output is with a first predetermined range.

6. The apparatus of claim 5, wherein said subtraction means subtracts an adjusted said portion from said sensor signal when said subtraction means output falls within a second predetermined range, said magnitude of said adjusted portion being a function of the magnitude of said subtraction means output.

7. The apparatus of claim 4, wherein said analyzing means is further for receiving said controlled portion of said signal.

8. A method of processing signals that contain information about the oxygen saturation of arterial blood flowing in tissue, said signals including a relatively periodic pulsatile component superimposed upon a slowly varying baseline component, said method comprising the steps of:

subtracting from said information signal a controlled portion of said information signal, the magnitude of said controlled portion being approximately equal to said baseline component and being determined by a subtraction control signal;

producing a subtraction output that is approximately equal to the periodic pulsatile component of the information signal remaining after said controlled portion is subtracted from said information signal; and producing said subtraction control signal, the magnitude of said subtraction control signal produced being a function of said subtraction output and indicating any adjustment to be made in said controlled portion subtracted from said information signal.

9. A method of processing signals, produced by a sensor, that contain information about the oxygen saturation of arterial blood flowing in tissue, said method comprising the steps of:

subtracting from said sensor signal a controlled portion of said signal to provide a remaining portion of said signal;

controlling the magnitude of said controlled portion of said signal based upon the magnitude of said remaining portion of said signal; and processing information about said controlled portion and said remaining portion of said signal to produce an indication of the oxygen saturation of said arterial blood flowing in said tissue.

* * * * *

UNITED STATES PATENT AND TRADEMARK OFFICE
CERTIFICATE OF CORRECTION

PATENT NO. : 4,892,101

DATED : January 9, 1990

INVENTOR(S) : Cheung et al.

It is certified that error appears in the above-identified patent and that said Letters Patent is hereby corrected as shown below:

| Column | Line | |
|---|---|---|
| 5 | 21 | "predetrmined" should be --predetermined-- |
| 6 | 36 | "ciruit" should be --circuit-- |
| 9 | 63 | "appareciated" should be --appreciated-- |
| 11 | 36 | "wavelengtcan" should be --wavelength can-- |
| 16 | 11 | "the" (second occurrence) should be --then-- |
| 21 | 63 | "Microputer" should be --microcomputer-- |
| 22 | 21 | "accuate" should be --accurate-- |
| 22 | 46 | "references" should be --Figures-- |
| 23 | 42 | "with" should be --within-- |

Signed and Sealed this

Fifteenth Day of December, 1992

*Attest:*

DOUGLAS B. COMER

*Attesting Officer*     *Acting Commissioner of Patents and Trademarks*